United States Patent
Kitaoka et al.

(10) Patent No.: US 9,314,357 B2
(45) Date of Patent: Apr. 19, 2016

(54) STENT FOR PLACEMENT IN LIVING BODY AND STENT DELIVERY SYSTEM

(75) Inventors: Takashi Kitaoka, Ashigarakami-gun (JP); Ryota Sugimoto, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 701 days.

(21) Appl. No.: 13/405,867

(22) Filed: Feb. 27, 2012

(65) Prior Publication Data

US 2012/0158119 A1    Jun. 21, 2012

Related U.S. Application Data

(63) Continuation of application No. PCT/JP2010/065637, filed on Sep. 10, 2010.

(30) Foreign Application Priority Data

Sep. 16, 2009    (JP) ................................. 2009-214984

(51) Int. Cl.
*A61F 2/90*          (2013.01)
*A61F 2/966*        (2013.01)
(Continued)

(52) U.S. Cl.
CPC . *A61F 2/966* (2013.01); *A61F 2/91* (2013.01); *A61F 2/915* (2013.01); *A61F 2/958* (2013.01); *A61F 2002/825* (2013.01); *A61F 2230/0054* (2013.01)

(58) Field of Classification Search
CPC .............. A61F 2/82; A61F 2/86; A61F 2/915

USPC ........................ 623/1.11, 1.15, 1.16
See application file for complete search history.

(56) References Cited

U.S. PATENT DOCUMENTS 5,807,327 A * 9/1998 Green et al. ................. 623/1.11
6,231,599 B1 * 5/2001 Ley .............................. 623/1.15
(Continued)

FOREIGN PATENT DOCUMENTS

CN          1434690 A      8/2003
CN      101151003 A      3/2008
(Continued)

OTHER PUBLICATIONS

International Search Report (PCT/ISA/210) issued on Oct. 19, 2010, by Japanese Patent Office as the International Searching Authority for International Application No. PCT/JP2010/065637.
(Continued)

*Primary Examiner* — Kathleen Holwerda
(74) *Attorney, Agent, or Firm* — Buchanan Ingersoll & Rooney PC

(57) ABSTRACT

A stent for placement in living body is substantially in a tubular form and includes a plurality of wave-shaped struts extending in the axial direction from one end to the other of the stent. The axially-extending wave-shaped struts are arranged in a circumferential direction, and connection struts interconnect the respective circumferentially adjacent wave-shaped struts. The circumferentially adjacent wave-shaped struts include a plurality of closer sections and farther sections. The connection struts interconnect between the closer sections of adjacent wave-shaped struts, and each has at the center thereof a bent portion extending in the axial direction of the stent.

19 Claims, 15 Drawing Sheets

(51) Int. Cl.
 *A61F 2/91* (2013.01)
 *A61F 2/915* (2013.01)
 *A61F 2/958* (2013.01)
 *A61F 2/82* (2013.01)

(56) References Cited

U.S. PATENT DOCUMENTS

| | | | |
|---|---|---|---|
| 6,302,893 B1 * | 10/2001 | Limon et al. | 606/108 |
| 6,309,414 B1 * | 10/2001 | Rolando et al. | 623/1.15 |
| 6,485,508 B1 | 11/2002 | McGuinness | |
| 6,565,598 B1 | 5/2003 | Lootz | |
| 6,818,013 B2 | 11/2004 | Mitelberg et al. | |
| 7,037,331 B2 | 5/2006 | Mitelberg et al. | |
| 7,311,726 B2 | 12/2007 | Mitelberg et al. | |
| 2001/0056298 A1 | 12/2001 | Brown et al. | |
| 2002/0049494 A1 * | 4/2002 | Schaldach et al. | 623/1.16 |
| 2003/0187494 A1 | 10/2003 | Loaldi | |
| 2004/0098094 A1 | 5/2004 | Boyle et al. | |
| 2004/0138730 A1 | 7/2004 | Mitelberg et al. | |
| 2005/0222191 A1 | 10/2005 | Falotico et al. | |
| 2006/0030922 A1 | 2/2006 | Dolan | |
| 2006/0085062 A1 * | 4/2006 | Lee et al. | 623/1.39 |

FOREIGN PATENT DOCUMENTS

| | | |
|---|---|---|
| EP | 1 095 632 A2 | 5/2001 |
| EP | 1197190 A2 | 4/2002 |
| EP | 1208814 A2 | 5/2002 |
| EP | 1 656 907 A1 | 5/2006 |
| EP | 1 872 741 A1 | 1/2008 |
| JP | 10-234860 A | 9/1998 |
| JP | 11-505441 A | 5/1999 |
| JP | 2002-505152 A | 2/2002 |
| JP | 2002513301 A | 5/2002 |
| JP | 2003-093519 A | 4/2003 |
| JP | 2005-289996 A | 10/2005 |
| JP | 2006-500173 A | 1/2006 |
| JP | 2008-508936 A | 3/2008 |
| JP | 2008546484 A | 12/2008 |
| WO | WO 96/26689 A1 | 9/1996 |
| WO | 9714375 A1 | 4/1997 |
| WO | 9822159 A2 | 5/1998 |
| WO | 2004/028340 A2 | 4/2004 |
| WO | 2007/002133 A2 | 1/2007 |
| WO | 2009018475 A1 | 2/2009 |

OTHER PUBLICATIONS

Office Action (Notification of Reasons for Refusal) issued on Jun. 17, 2014, in corresponding Japanese Patent Application No. 2011-531911, and an English translation of the Office Action. (16 pgs).
Office Action (Notification of First Office Action) issued on Jan. 22, 2014, by the State Intellectual Property Office of P.R. China in corresponding Chinese Patent Application No. 201080023380.0, and an English Translation of the Office Action. (24 pages).
Communication Pursuant to Article 94(3) EPC, dated Jul. 23, 2013, issued by the European Patent Office in corresponding European Patent Application No. 10 817 122.4-1651. (6 pages).
Extended European Search Report dated Oct. 26, 2012, issued in corresponding European Patent Application No. 10817122.4-1257/ 2444033 (8 pages).
Office Action issued by the Japan Patent Office on Nov. 12, 2014 in corresponding Japanese Application No. 2011-531911, and English language translation of Office Action (8 pages).
Office Action (Notification of the Second Office Action) issued on Aug. 15, 2014, by the State Intellectual Property Office of P.R. China in corresponding Chinese Patent Application No. 201080023380.0, and an English Translation of the Office Action (23 pages).

* cited by examiner

STENT FOR PLACEMENT IN LIVING BODY AND STENT DELIVERY SYSTEM

This application is a continuation of International Application No. PCT/JP2010/065637 filed on Sep. 10, 2010, and claims priority to Japanese Application No. 2009-214984 filed on Sep. 16, 2009, the entire content of both of which is incorporated herein by reference.

TECHNICAL FIELD

This present invention relates to a stent for placement in a living body and a stent delivery system for improving a stenosed or occluded portion of a living body lumen such as a blood vessel, bile duct, trachea, esophagus, urethra, etc.

BACKGROUND DISCUSSION

A stent for placement in living body is a generally tubular medical device which, for treatment of various diseases caused by stenosis or occlusion of a blood vessel or other living body lumen, is indwelled in the stenosed or occluded portion of the living body lumen so that the portion is dilated to secure the lumen.

An application involving use of the stent in a blood vessel is now described as an example, though the use of the stent is not limited in this regard.

A stent is inserted from outside into the inside of a living body, for which the stent is so designed as to be made relatively small in diameter (contracted state) at the time of insertion and to be expanded at an intended stenosed or occluded portion to achieve an enlarged diameter and maintain the lumen in an open state.

The usual practice is to use, as a stent, metallic wires or pipes processed into a cylindrical form. A stent is mounted on a catheter or the like in a radially reduced state, inserted into a living body, and expanded at an intended portion or the desired site in the lumen of the living body by some sort of method, thereby allowing the stent to be fixed in position close contact with the inner walls of the lumen and thus the shape of the lumen to be maintained. Stents are classified into self-expandable stents and balloon-expandable stents depending on the function and the manner of indwelling. A balloon-expandable stent has no expandable function by itself. After insertion of the balloon-expandable stent mounted on the balloon into the intended portion, the balloon is dilated or inflated so that the stent expands (or plastically deformed) by the action of the dilation force of the balloon, thereby permitting the stent to be fixed in close contact with the inner surfaces of the intended lumen. This type of stent needs the stent-expanding operations as mentioned above.

On the other hand, a self-expandable stent is one imparted with a self-expanding function in itself. This self-expandable stent is accommodated in a sheath in a radially contracted state and inserted into a living body, under which as soon as the stent is released from the sheath at an intended portion or desired site, it returns to an original expanded state by itself and is fixed in close contact with the inner walls of the lumen, thereby maintaining the shape of the lumen.

The current purpose of indwelling a stent is to return a blood vessel stenosed or occluded for some reason(s) to its original state of patency, mainly to prevent or reduce restenosis, which might occur after such a procedure as of PTCA in most cases. In recent years, in order to suppress the probability of restenosis to a greater extent, a drug-eluting stent having a drug such as an immunosuppressor or anticancer drug loaded thereon is used as well, and its effect is generally known.

On the other hand, as to the treatment of acute coronary syndromes, typical of which are acute myocardial infarction and unstable angina, or the treatment of unstable plaque that has been accepted as a preclinical stage thereof, no method therefor has been established yet. With respect to the treatment of acute coronary syndromes, almost all of existing stents and drug-eluting stents remain contraindicated. This is for the reason that if a stent is indwelled in a blood vessel containing a large amount of thrombi, the risks of stent malapposition and long-term thrombosis are undeniable.

With regard to the unstable plaque, MELER et al (Heart 2004; 90: 1395-1398: Plaque Sealing by Coronary Angioplasty) have proposed the concept of plaque sealing, in which the plaque is stabilized by giving a stimulus to its surface such as by balloon dilation. Recently, it has been reported that plaque sealing is carried out by use of a self-expandable stent having a relatively weak expansion force instead of a balloon.

Most of the self-expandable stents are employed in peripheral regions such as blood vessels of inferior limbs and carotid arteries, and, in the coronary region, the Radius stent alone, made by Boston Scientific Corporation, was previously introduced into the market. This stent has a form such as shown in JP-T-H11-505441 and International Application Publication No. WO96/26689. In this type of stent, stent indwelling positioning is more difficult than in the case of balloon-expandable stents in view of the properties of the stent, and it has been reported that there occurs a so-called jumping phenomenon in which the stent is unintentionally released from the sheath and indwelled.

It has been reported in academic conferences that when conventional balloon-expandable stents and self-expandable stents having a strong expansion force have been used in plaque sealing, there is the danger of rupturing the plaque owing to the stent indwelling operations themselves; and once the plaque has been ruptured, there is concern that a risk of peripheral occlusion and an increased inflammatory reaction thereat may occur and thus, such stents are unsuited for the plaque sealing.

Another type of stent has been proposed as described in Japanese Application Publication No. 2003-93519, U.S. Pat. No. 6,818,013, U.S. Pat. No. 7,037,331, and U.S. Pat. No. 7,311,726.

The stent disclosed in this patent literature includes a plurality of wave-shaped struts extending in an axial direction from one end side to the other end side of a stent and arranged in a circumferential direction of the stent, and a plurality of connection struts that interconnect the respective adjacent wave-shaped struts to each other and extend over a predetermined length, wherein the end portions of the respective wave-shaped struts join to the end portions of the adjacent wave-shaped struts. Since this stent is made of plural wave-shaped struts extending in the axial direction of the stent, the stent is flexible and has the possibility of application to the plaque sealing.

The connection struts of the stent described in Japanese Application Publication No. 2003-93519, U.S. Pat. No. 6,818,013, U.S. Pat. No. 7,037,331, and U.S. Pat. No. 7,311,726 extend in an axial direction while curving. According to our studies, we have found that this construction of the stent, including the connection struts extending in the disclosed manner, results in deformability under compression in a radial direction that is not satisfactory and an expansion force that is also not satisfactory.

SUMMARY

The stent disclosed here by way of several embodiments described as examples is configured for placement in a living body, is substantially tubular in form, and includes a plurality of wave-shaped struts extending in an axial direction from one end side to the other end side of the stent and arranged in a circumferential direction of the stent, and a plurality of connection struts interconnecting the respective adjacent wave-shaped struts, wherein the adjacent wave-shaped struts are provided with a plurality of closer sections and farther sections, and the connection struts interconnect the adjacent wave-shaped struts between the closer sections thereof and each connection section has at the center thereof a bent portion extending in the axial direction of the stent.

The stent exhibits good deformability in the radial direction while still using wave-shaped struts extending in an axial direction of the stent and which have an adequate expansion force.

The bent portion of the connection strut can be a free end extending in the direction of the distal end of the stent.

The plurality of wave-shaped struts can be configured to include a plurality of first wave-shaped struts having a plurality of upper points and a plurality of lower points and a plurality of second wave-shaped struts having a plurality of upper points and a plurality of lower points and each provided between the respective first wave-shaped struts, the respective adjacent first wave-shaped strut and second wave-shaped strut form the closer section by permitting the upper point or lower point of one wave-shaped strut and the lower point or upper point of the adjacent other wave-shaped strut to be set substantially in face-to-face relation with each other, and the connection strut interconnects the upper point or lower point of the first-wave-shaped strut and the lower point or upper point of the second wave-shaped strut, which form the closer section.

The circumferentially adjacent first wave-shaped struts and second wave-shaped struts form the farther sections by permitting the lower point or upper point of one wave-shaped strut and the upper point or lower point of the circumferentially adjacent other wave-shaped strut to be positioned substantially in face-to-face relation with each other, with the bent portion of the connection strut is located in the vicinity of the farther section.

The stent can be configured so that substantially all of the closer sections of the adjacent first wave-shaped strut and second wave-shaped strut are interconnected with the connection struts.

The first wave-shaped struts, respectively, can be configured to possess substantially the same waveform except for the end portions. The second wave-shaped struts, respectively, can also be configured to possess substantially the same waveform except for the end portions.

In addition, the first wave-shaped struts and the second wave-shaped struts can be configured to possess substantially the same wavelength and substantially the same amplitude, with the second wave-shaped struts being shifted, relative to the first wave-shaped struts, by about half a wavelength in the axial direction of the stent.

The first and second wave-shaped struts preferably extend substantially parallel to the central axis of the stent.

The connection struts connecting each pair of circumferentially adjacent wave-shaped struts extend in a linear fashion along an axial direction of the stent. The connection struts are preferably also arranged as a plurality of connection struts extending along the circumferential direction of the stent.

The stent preferably also includes arcuate or small curved portions in the vicinity of the connection portion between the wave-shaped strut and the connection strut.

The stent can also be configured to have a surface which promotes endothelialization.

According to one alternative, the stent possesses a substantially cylindrical form, is compressed in a direction of a central axis when inserted into a living body, and is expanded outwardly when indwelled in the living body so that the stent is restored to its original pre-compression form.

The stent can alternatively be substantially tubular in form, have an outer diameter permitting insertion into a lumen in a living body, and is expanded when a force radially spreading from inside of the stent is exerted on the stent.

Another aspect disclosed here involves a stent for placement in living body, wherein the stent comprises: a plurality of axially extending wave-shaped struts which are circumferentially arranged in a substantially cylindrical form, with each of the plurality of wave-shaped struts extending in an axial direction from one axial end of the stent to an opposite axial end of the stent; and a plurality of connection struts interconnecting the axially extending wave-shaped struts which are circumferentially adjacent. The connection struts each have a center. Each of the axially extending wave-shaped struts possesses a plurality of alternating and axially spaced apart points, and the points include upper points which are mountains of the wave-shaped strut, and lower points which are valleys of the wave-shaped strut. The points on each of the axially extending wave-shaped struts are circumferentially aligned with points on others of the axially extending wave-shaped struts, and at least some of the circumferentially aligned points in each pair of the circumferentially adjacent wave-shaped struts are located in closer sections of the stent, while at least some of the circumferentially aligned points in each pair of the circumferentially adjacent wave-shaped struts are located in farther sections of the stent. The points of the circumferentially adjacent wave-shaped struts located in the closer sections are positioned closer together than the points of the circumferentially adjacent wave-shaped struts located in the farther sections. Each connection strut interconnects the axially extending wave-shaped struts at the closer section. A bent portion is provided at the center of each connection section, and the bent portions of each connection section extend in the axial direction of the stent.

According to another aspect, a stent delivery system includes a sheath, a stent such as described above accommodated in the distal end portion of the sheath, and an inner tube slidably inserted into the sheath and configured to release the stent from the distal end of the sheath by movement toward a proximal end side of the sheath. The stent used in the stent delivery system can be compressed in a direction of a central axis when the sheath is moved toward the distal end side relative to the stent and is able to be accommodated in the distal end portion of the sheath.

The stent delivery system can also be configured to include a tubular shaft body, a foldable and dilatable balloon provided at a distal end portion of the shaft body, and a stent such as described above which is disposed so as to enclose the balloon of a folded state and is expanded by dilation of the balloon.

DETAILED DESCRIPTION

Figure 1:
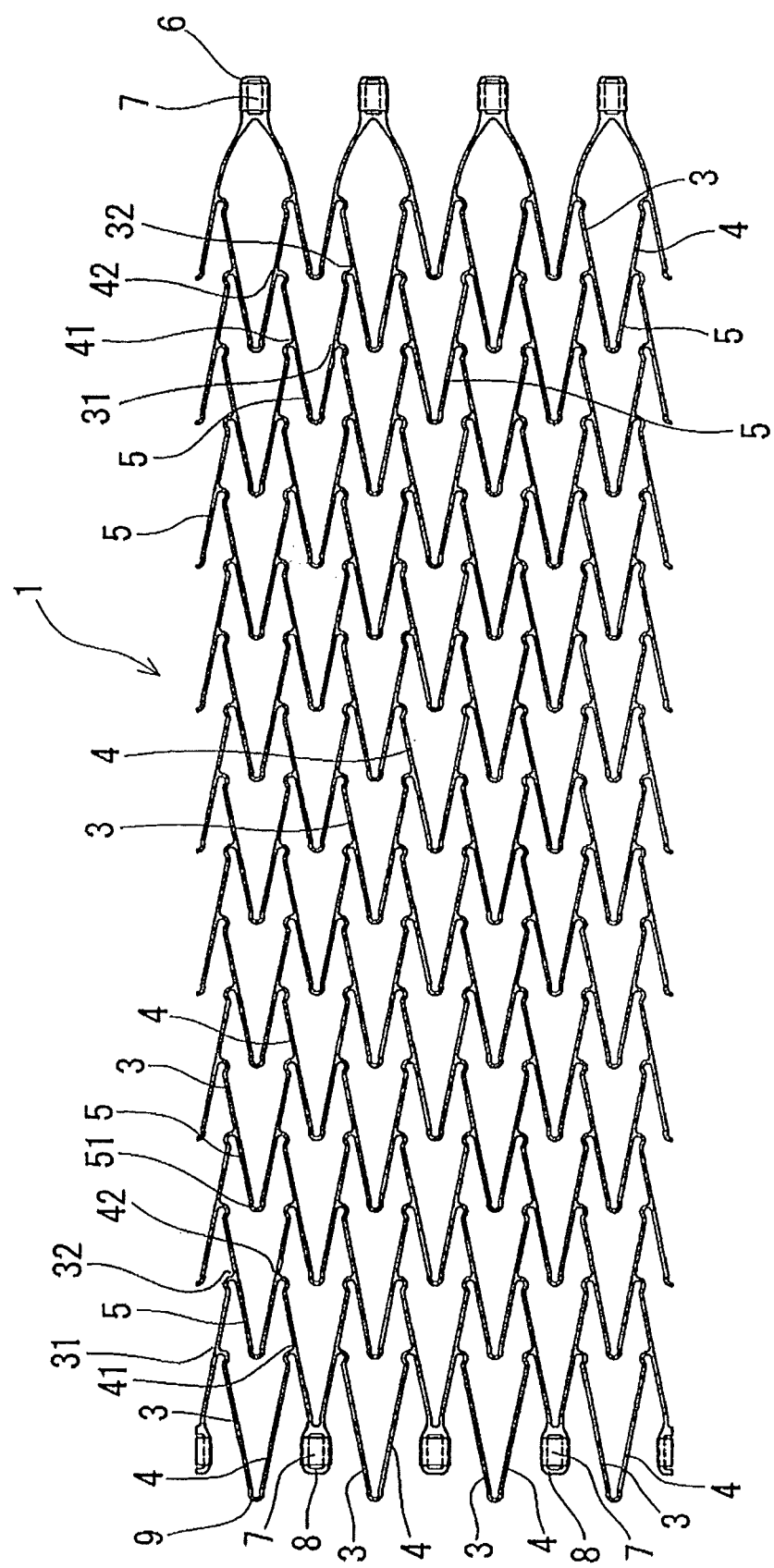
FIG. 1 is a development view of a stent for placement in living body according to one embodiment disclosed here by way of example.
Figure 2:
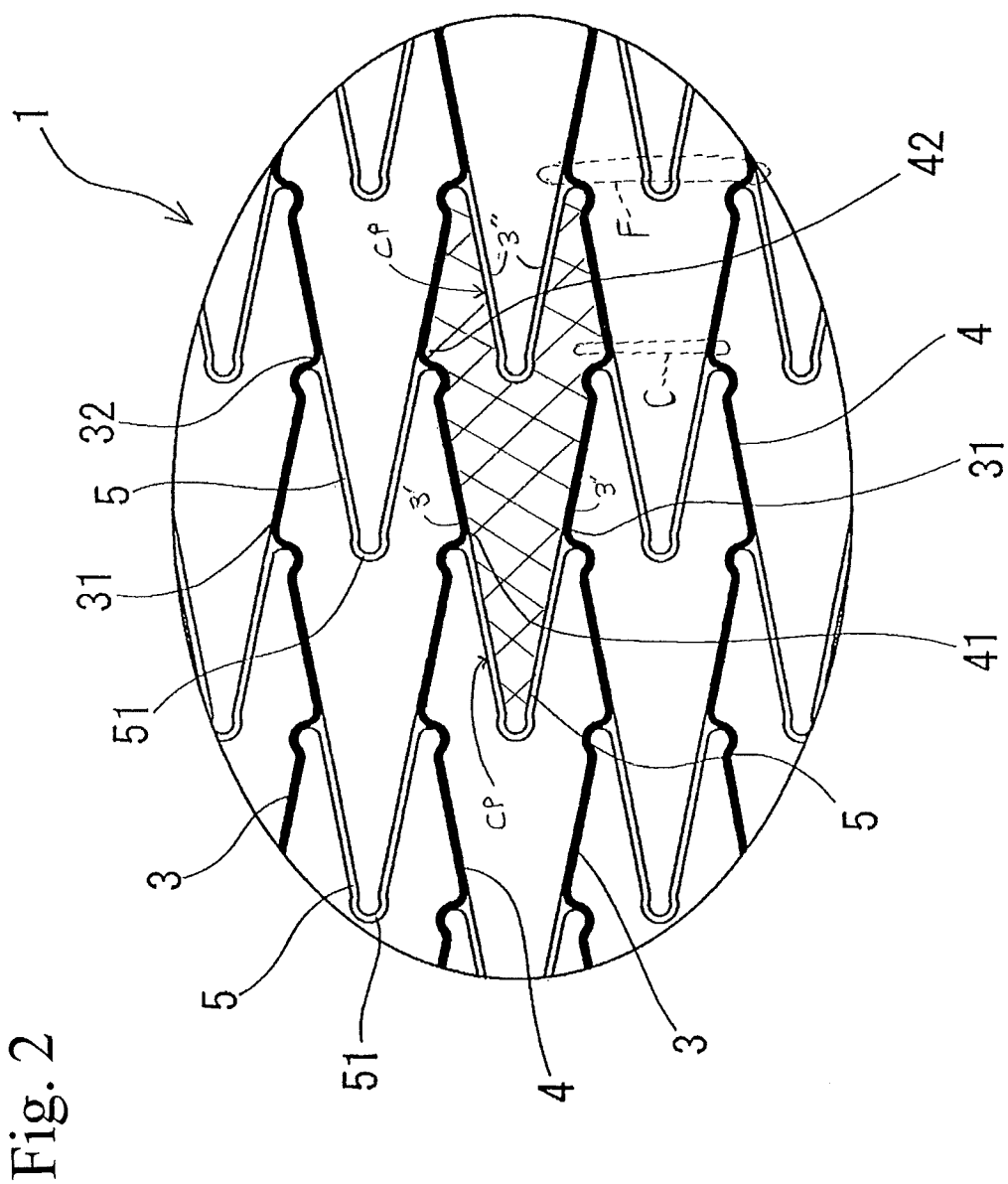
FIG. 2 is a partially enlarged view of a portion of the stent shown in FIG. 1.

Referring initially to FIGS. 1 and 2, the stent 1 for placement in a living body according to one embodiment is possesses a substantially tubular form. The stent 1 is provided with a plurality of wave-shaped struts 3 and 4 extending from one end side to the other end side of the stent 1 in an axial direction and arranged along a circumferential direction of the stent, and a plurality of connection struts 5 interconnecting the respective adjacent wave-shaped struts 3 and 4. The adjacent wave-shaped struts 3 and 4 are provided with a plurality of closer sections and a plurality of farther sections, and the connection struts 5 each interconnect the adjacent wave-shaped struts 3 and 4 at the closer sections and are provided at a central portion thereof with a bent portion 51 extending toward the axial direction of the stent.

More specifically, in this embodiment of the stent 1 for placement in living body, the plurality of wave-shaped struts 3 and 4 include a plurality of first wave-shaped struts 3 each having a plurality of upper points 31 (peaks) and a plurality of lower points 32 (valleys), and a plurality of second wave-shaped struts 4 each having a plurality of upper points 42 (peaks) and a plurality of lower points 41 (valleys), with each of the second wave-shaped struts 4 being located between circumferentially adjacent first wave-shaped struts 3. The respective adjacent first wave-shaped struts 3 and second wave-shaped struts 4 are so configured that the upper point or lower point of one wave-shaped strut is substantially in face-to-face relation with the lower point or upper point of the other wave-shaped strut, thereby forming a closer section. The connection strut 5 interconnects the upper point 31 or lower point 32 of the first wave-shaped strut 3 and the lower point 41 or upper point 42 of the second wave-shaped strut 4, both of which form the closer section. The respective circumferentially adjacent first wave-shaped struts 3 and second wave-shaped struts 4 are so configured that the lower point or upper point of one wave-shaped strut is substantially in face-to-face relation with (circumferentially aligned with) the upper point or lower point of the other wave-shaped strut, thereby forming a farther section. The closer sections are those sections of the stent where an upper/lower point of one of the wave-shaped struts 3, 4 is circumferentially closest to the facing upper/lower point of the other wave-shaped strut 3, 4. The farther sections are those sections of the stent where an upper/lower point of one of the wave-shaped struts 3, 4 is circumferentially farther from the facing upper/lower point of the other wave-shaped strut 3, 4. In other words, in the closer sections, the upper/lower points of the struts 3, 4 that face one another are circumferentially closer to each other than the upper/lower points of the struts 3, 4 that face one another in the farther sections. One each of the closer sections C and the farther sections F is identified by way of example in FIG. 2.

The stent 1 according to this embodiment is substantially cylindrically shaped and is a so-called self-expandable stent wherein when inserted in living body, the stent is compressed toward the central axis and is externally expanded when indwelled in living body thereby automatically being restored to its form or shape before compression. The stent may be a so-called balloon-expandable stent in which the stent is a substantially tubular body, has a diameter sufficient for insertion in the living body lumen and is expandable outwardly when a spreading or expanding force from the inside of the tubular body toward a radially outward direction is exerted on the stent. The stent 1 according to this embodiment is made from a metallic pipe of a determined diameter and expanded, followed by thermal treatment.

To describe the stent in more detail, the stent 1 according to this embodiment includes, as shown in FIG. 1, a plurality of the first wave-shaped struts 3 extending in the axial direction from one axial end to the opposite axial end of the stent 1 and arranged along and spaced apart along a circumferential direction of the stent, a plurality of the second wave-shaped struts 4 extending in the axial direction from one axial end to the opposite axial end of the stent 1 and arranged along and spaced apart along a circumferential direction of the stent, and a plurality of the connection struts 5 interconnecting the two wave-shaped struts 3, 4 and extending along the axial direction over a predetermined length.

The first wave-shaped struts 3 extend in the axial direction substantially parallel to the central axis of the stent. The plural first wave-shaped struts 3 are arranged or spaced apart from one another along the circumferential direction of the stent. The number of the first wave-shaped struts 3 is preferably three or more, more preferably three to eight. In addition, it is preferred that a plurality of the first wave-shaped struts 3 are arranged substantially equiangularly relative to the central axis of the stent (i.e., the first wave-shaped stents are spaced at substantially equal angular intervals in the circumferential direction).

With the stent 1 according to this embodiment, the first wave-shaped struts 3 are of a sequence of substantially the same waveforms over a predetermined length except for both axial end portions. In other words, all of the first wave-shaped struts 3 have substantially the same waveform except in the vicinity of the two end portions, i.e. they are in a sequence of waves of the same wavelength and same amplitude. In case where the first wave-shaped struts 3 have substantially the same waveform along their entire length, the wavelength thereof is preferably at 0.5 to 0.8 mm, more preferably at 2.0 to 4.0 mm and the amplitude is preferably at 0.1 to 10.0 mm, more preferably at 0.3 to 3.0 mm although differing depending on the outer diameter of the stent.

The second wave-shaped struts 4 also extend in the axial direction substantially parallel to the central axis of the stent. The second wave-shaped struts 4 are arranged along the circumferential direction of the stent, and the second wave-shaped struts 4 are each provided between circumferentially adjacent pairs of the first wave-shaped struts 3. The number of the second wave-shaped struts 4 is preferably three or more, more preferably three to eight. In addition, it is preferred that the second wave-shaped struts 4 are arranged substantially equiangularly relative to the central axis of the stent (i.e., the second wave-shaped stents are spaced at substantially equal angular intervals in the circumferential direction). The number of second wave-shaped struts is the same as the number of first wave-shaped struts.

With the stent 1 according to this embodiment, the second wave-shaped struts 4 are of a sequence of substantially the same waveforms over a predetermined length except for both end portions. In other words, the second wave-shaped struts 4 have substantially the same waveform except in the vicinity of the two end portions, i.e. they are in a sequence of waves of the same wavelength and same amplitude. In case where the second wave-shaped struts 4 have substantially the same waveform along their entire length, the wavelength thereof is preferably at 0.5 to 8.0 mm, more preferably at 2.0 to 4.0 mm and the amplitude is preferably at 0.1 to 10.0 mm, more preferably at 0.3 to 3.0 mm although differing depending on the outer diameter of the stent.

In this embodiment, the first wave-shaped struts 3 and the second wave-shaped struts 4 each possess a triangular waveform.

Further, with the stent 1 according to this embodiment, the first wave-shaped struts 3 and the second wave-shaped struts 4, respectively, have substantially the same waveform. More particularly, with the stent 1 according to the embodiment, the first wave-shaped struts 3 and the second wave-shaped struts 4, respectively, have substantially the same wavelength and substantially the same amplitude. The second wave-shaped struts 4 are, respectively, shifted by about half a wavelength in the axial direction of the stent relative to the first wave-shaped struts 3.

Hence, as shown in FIGS. 1 and 2, adjacent first wave-shaped struts 3 and second wave-shaped struts 4 are so configured that the upper point 31 or lower point 32 of the first wave-shaped strut 3 and the lower point 41 or upper point 42 of an adjacent second wave-shaped strut 4 are substantially facing each other, thereby forming the closer sections and the farther sections. In other words, with this stent 1, the adjacent first wave-shaped strut 3 and second wave-shaped strut 4 are arranged such that the upper points of the two struts 3, 4 do not face each other, and the lower points of the two struts 3, 4 do not face each other, and so the closer sections and farther sections are alternately established along the axial direction.

In the stent according to this embodiment, the respective wave-shaped struts 3 and 4 all have the same length except for the two ends of the struts. Accordingly, when the stent is axially compressed, the struts come close to parallel to the axial direction, and diameter reduction proceeds relatively smoothly without axial stretching since the struts have the same length. With the stent according to this embodiment, the respective wave-shaped struts 3 and 4 are arranged equiangularly relative to the central axis of the stent except for the two ends. Therefore, when the stent is compressed along the radial direction, the spaces between the struts become uniformly small, thereby allowing the stent to be well contracted without causing overlapping of the struts.

As shown in FIGS. 1 and 2, the stent 1 has the connection struts 5 which interconnect the circumferentially adjacent wave-shaped struts 3 and 4 between the closer sections thereof and which has, at a center thereof, a bent portion 51 extending along the axial direction of the stent. The axial length of the connection strut 5 is preferably at 0.1 to 3.0 mm, more preferably at 0.5 to 2.0 mm, although differing depending on the outer diameter of the stent. The connection strut 5 is symmetrical with respect to the central axis of the stent 1 and the apex of the bent portion 51. With the stent 1 according to this embodiment, substantially all of the plurality of closer sections formed between the respective adjacent first wave-shaped struts 3 and second wave-shaped struts 4 are interconnected with the connection struts 5. The bent portion 51 of the connection strut 5 is located in the vicinity of the farther section formed between the wave-shaped struts 3 and 4. The bent portion 51 of the connection strut 5 is a free end extending in a direction of the distal end of the stent 1. With stent 1 according to this embodiment, a plurality of the connection struts 5 are provided between each pair of circumferentially adjacent wave-shaped struts 3, 4 and are arranged linearly along the axial direction of the stent. There are thus a plurality of the connection struts 5 arranged linearly along the lengthwise extent of the stent between circumferentially adjacent wave-shaped struts 3, 4, and a plurality of connection struts 5 arranged along the circumferential direction or circumferential extent of the stent.

The distal end portion of the stent 1 according to this embodiment is provided with a bent portion 9, formed by combining the distal end portions of the first wave-shaped strut 3 and the second wave-shaped strut 4, and a bulge portion 8 provided at the bent portion 51 of the connection strut 5. The bent portion 9 and the bulge portion 8 are alternately arranged along the circumferential direction. This bulge portion 8 is attached with a radiopaque marker 7 described below. The bent portion 9 is located beyond (axially beyond) the bulge portion 8 on the distal end of the stent. Thus, the radiopaque marker at the distal end side is positioned at a slightly inner side from the axial end-most part of the stent. Since the struts are provided outside of the marker or axially beyond the marker, a lesion can be reliably covered.

The stent 1 according to this embodiment is arranged at the proximal end portion thereof in such a way that the proximal end portions of the first wave-shaped struts 3 and the second wave-shaped struts 4 are all connected to connection portions 6 and thus has no free end except for the connection sections 6. With the stent 1 according to this embodiment, no free end facing toward the direction of the proximal end of the stent is included except for the connection sections 6. In other words, all the bent portions are facing toward the distal end relative to the stent. This means that when the sheath is moved toward the distal end of the stent, the stent can be re-accommodated in the sheath (stent accommodation member) without susceptibility to the stent catching the sheath because of the lack of a free end facing toward the sheath (stent accommodation member).

FIG. 1 shows the radiopaque marker 7 provided at the connection portions 6. In this embodiment, the connection portion 6 is provided with two frames extending toward the end portion and extending parallel to each other at a predetermined distance therebetween, and the radiopaque marker 7 covers the two frames substantially wholly or partially. The radiopaque marker 7 is in the form of a thin rectangular parallelepiped, which includes therein two frames and is recessed at a central portion thereof, thus being fixed with the two frames. The material for forming the radiopaque marker favorably includes, for example, one (elemental substance) or two or more (alloy) of elements selected from the group having iridium, platinum, gold, rhenium, tungsten, palladium, rhodium, tantalum, silver, ruthenium, and hafnium. The length of the marker is preferably at 0.1 to 4.0 mm, more preferably at 0.3 mm to 1.0 mm. The thickness of the marker is preferably at 0.01 to 0.30 mm, more preferably at 0.03 to 0.10 mm. The end portion of the connection portion 6 at one end side is formed with an engaging hole. The engaging hole preferably has a diameter of 0.01 to 0.30 mm, more preferably 0.05 to 0.20 mm.

This stent 1 is inserted into a living body from the distal end side (or the side of the bent portion 9) and indwelled.

The stent 1 according to this embodiment is arranged such that closed linear bodies of a deformed hexagon (an example of which is shown by cross-hatching in FIG. 2), in which distal end side struts 3', each of which has a free end of the bent portion 51 extending toward the distal end side of the stent, and proximal end side struts 3", each of which has two bent portions 32 and 42 (41 and 31) extending toward the proximal end side of the stent and one bent portion 51 extending toward the distal end side of the stent between the two bent portions, are connected at two connection points 31 and 41 (42 and 32) extending along the circumferential direction of the stent, have partial common portions CP and are arranged in plural, linearly along the axial direction of the stent. In the individual closed linear bodies arranged in the axial direction of the stent, the distal end side relative to the central portion of the distal end side strut of one linear body and the bent portion (the above-mentioned connection strut 5) extending toward the distal end side of the stent between the two bent portions 32 and 42 (41 and 31) of the proximal end side strut of the other linear body establish the common portion. The closed linear bodies each have the partial common portion and are arranged plural in number in a zigzag form along the circumferential direction of the stent. The closed linear bodies arranged along the circumferential direction of the stent are such that the adjacent two closed linear bodies in the respective circumferential directions have a common portion. In the respective closed linear bodies arranged in the circumferential direction of the stent, a section ranging from the connection points (31, 32, 41, and 42) between the distal end side strut and the proximal end side strut of one closed linear body to the vicinity of the apexes (31, 32, 41, and 42) of the bent portions extending to the stent proximal end side of the proximal end side strut, and a section ranging from the vicinity of the central portion of the distal end side strut of the other closed linear body to the connection points (31, 32, 41, and 42) between the distal end side strut and the proximal end side strut establish the common portion. The closed linear body is connected to the struts for the other closed linear body at the vicinity of the apexes of the two bent portions extending toward the stent proximal end side of the proximal end side strut and also at the two connection points between the distal end side struts and the proximal end side struts, and these points are designed not to form a free end, respectively.

Further, with the stent 1 according to this embodiment, an arcuate or small curved portion is provided in the vicinity of the connection portion of the wave-shaped struts 3 and 4 and the connection strut 5. With the stent 1 according to this embodiment, the upper points 31 and 42 and the lower points 32 and 41, which constitute the closer sections of the first wave-shaped strut 3 and the second wave-shaped strut 4 to be connected with the connection strut 5, are each shaped in an arcuate or small curved portion (portion of a circle) extending slightly in the circumferential direction and in a direction away from the connection strut 5.

Figure 3:
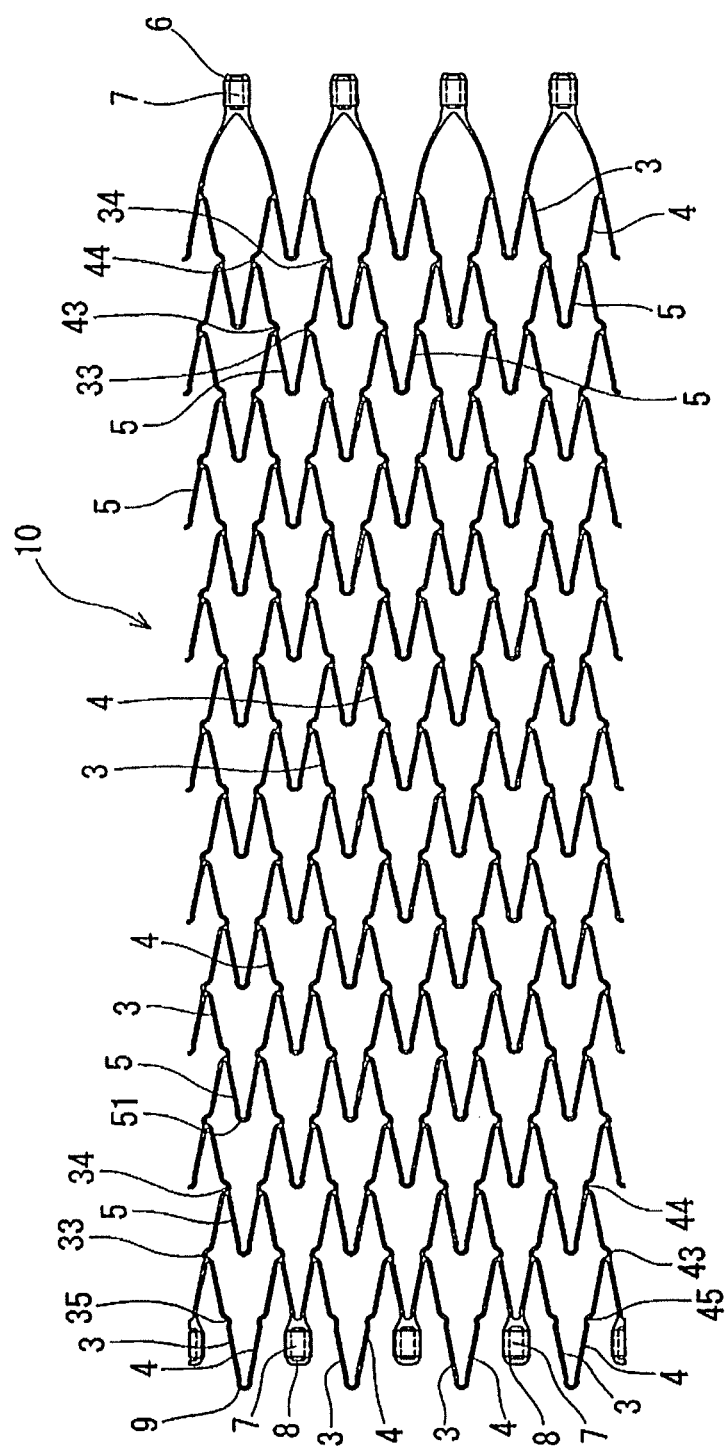
FIG. 3 is a development view of a stent for placement in living body according to another embodiment disclosed here by way of example.
Figure 4:
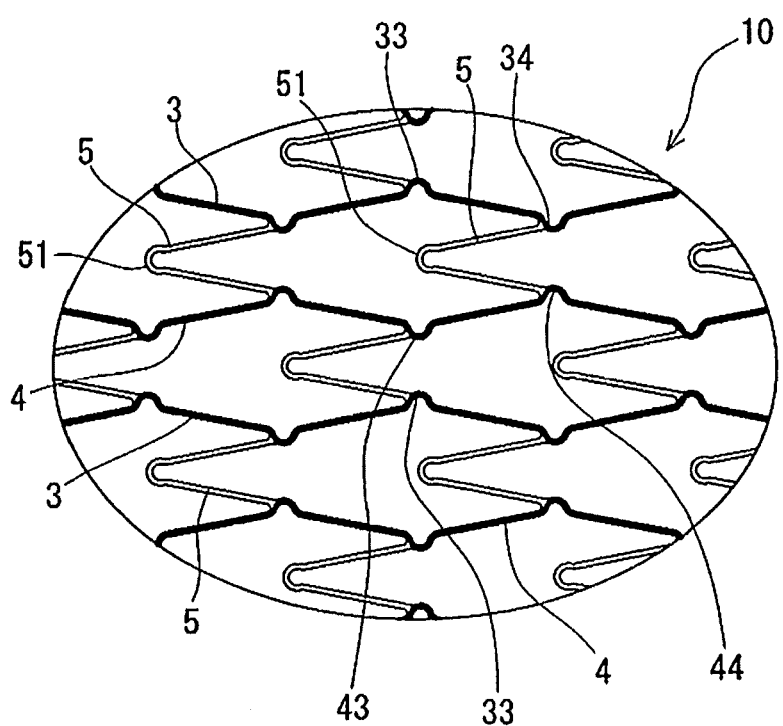
FIG. 4 is a partially enlarged view of a portion of the stent shown in FIG. 3.

FIGS. 3 and 4 illustrate a stent 10 for placement in living body according to another embodiment. The difference between the stent 10 according to this embodiment and the above-described stent 1 resides only in the form or configuration of the arcuate or small curved portion. Other features of the stent according to this embodiment which are the same as in the above-described embodiments are identified by common reference numerals, and a detailed description of such features is not repeated. The stent 10 according to this embodiment includes arcuate or small curved portions provided at a connection portion between the wave-shaped struts 3 and 4 and the connection strut 5. In the stent 10 according to this embodiment, the upper points 33, 44 and the lower points 34, 43, constituting the closer sections of the first wave-shaped strut 3 and the second wave-shaped strut 4 to which the connection strut 5 is interconnected, are formed as an arcuate or small curved portion (portion of a circle) curved in a circumferential direction and also in a direction of approximation to the connection strut 5 to be connected. The end portion of the connection strut 5 is connected to this arcuate or small curved portion.

The stent 10 according to this embodiment also includes arcuate portions or small curved portions 35, 45, each curved inwardly of a bent portion 9 and located on the proximal side by a predetermined distance relative to the bent portion 9 which is formed by connecting the distal end portions of the first wave-shaped strut 3 and the second wave-shaped strut 4. The whole expansion retention force of the bent portion 9 formed as a long free end can thus be improved.

Figure 5:
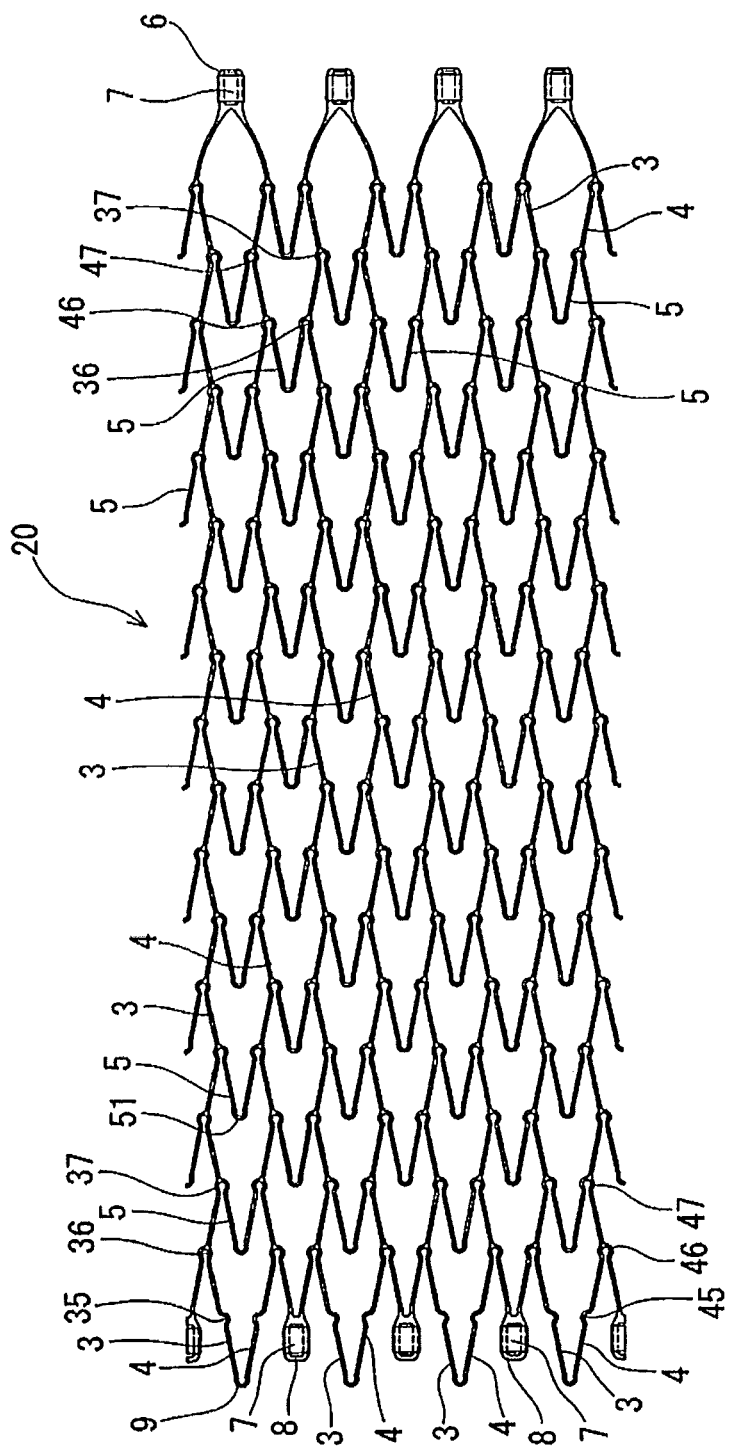
FIG. 5 is a development view of a stent for placement in living body according to a further embodiment disclosed here by way of example.
Figure 6:
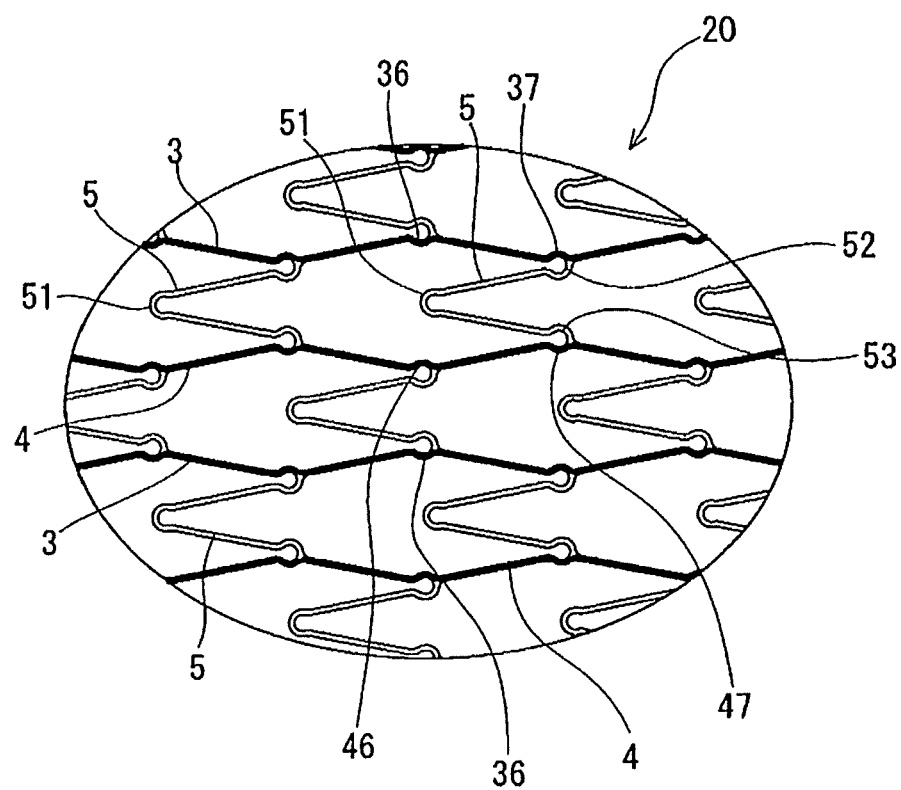
FIG. 6 is a partially enlarged view of a portion of the stent shown in FIG. 5.

FIGS. 5 and 6 illustrate a stent 20 for placement in a living body according to a further embodiment. The difference between the stent 20 of this embodiment and the above-stated stent 1 resides only in the form or configuration of the arcuate or small curved portion. Other features of the stent according to this embodiment which are the same as in the above-described embodiments are identified by common reference numerals, and a detailed description of such features is not repeated. With the stent 20 according to this embodiment, the arcuate or small curved portion is provided at a connection portion between the wave-shaped struts 3 and 4 and the connection strut 5. More specifically, the stent 20 according to this embodiment includes the upper and lower points of the first wave-shaped strut 3 and the upper and lower points of the second wave-shaped strut 4, to which the connection struts 5 are connected, in the form of arcuate portions or small curved portions (portions of a circle) 36, 37, 46, 47, which are curved slightly in the circumferential direction and also in the direction away from the connection strut 5. The stent 20 according to this embodiment is also configured so that both end portions 52, 53 of the connection struts 5 connected to the wave-shaped struts 3 and 4 are in the form of an arcuate portion or small curved portion (portion of a circle) curved in an inward direction of the connection strut 5. The small curved portions 36, 37, 46, 47 of the wave-shaped struts 3 and 4 and the small curved portions 52, 53 of the connection struts 5 are connected together thereby forming arcuate or small curved portions.

The stent 20 according to this embodiment also includes the arcuate or small curved portions 35, 45 curved inwardly of the bent portion 9 on the proximal side by a predetermined distance relative to the bent portion 9 which is formed by combining the distal portions of the first wave-shaped strut 3 and the second wave-shaped strut 4.

Figure 7:
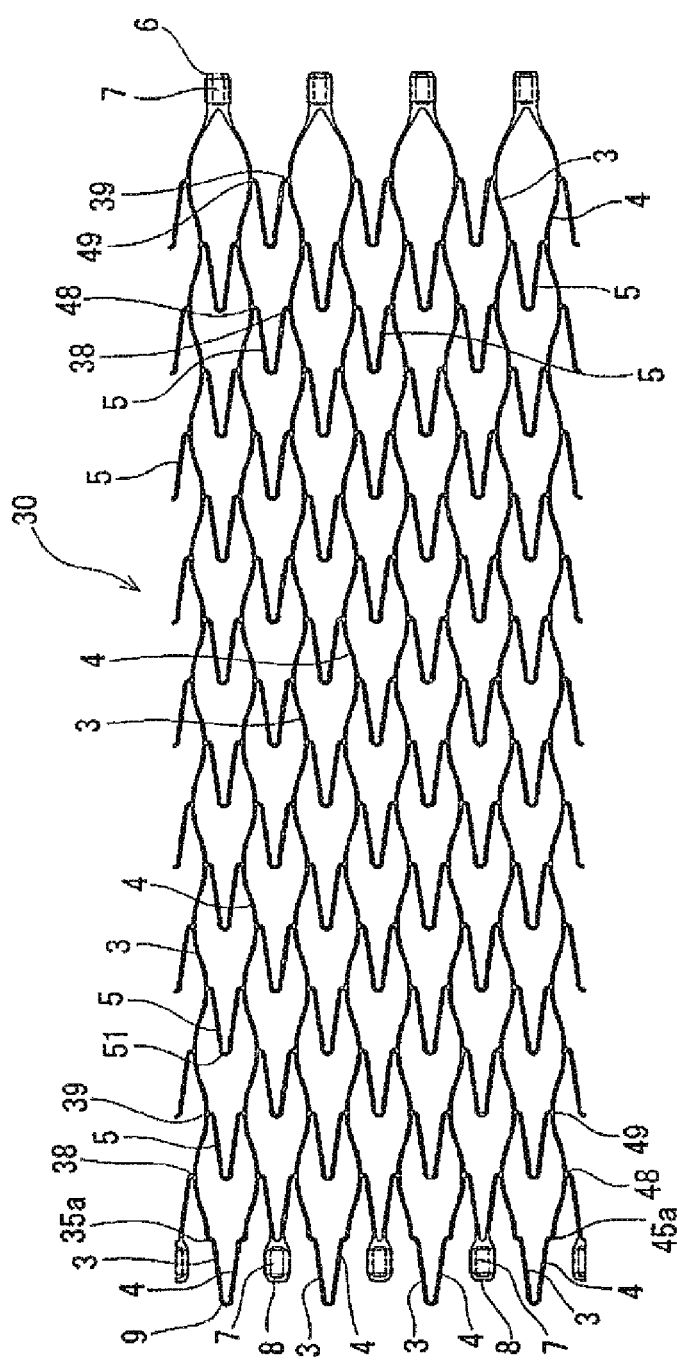
FIG. 7 is a development view of a stent for placement in living body according to yet another embodiment disclosed here by way of example.
Figure 8:
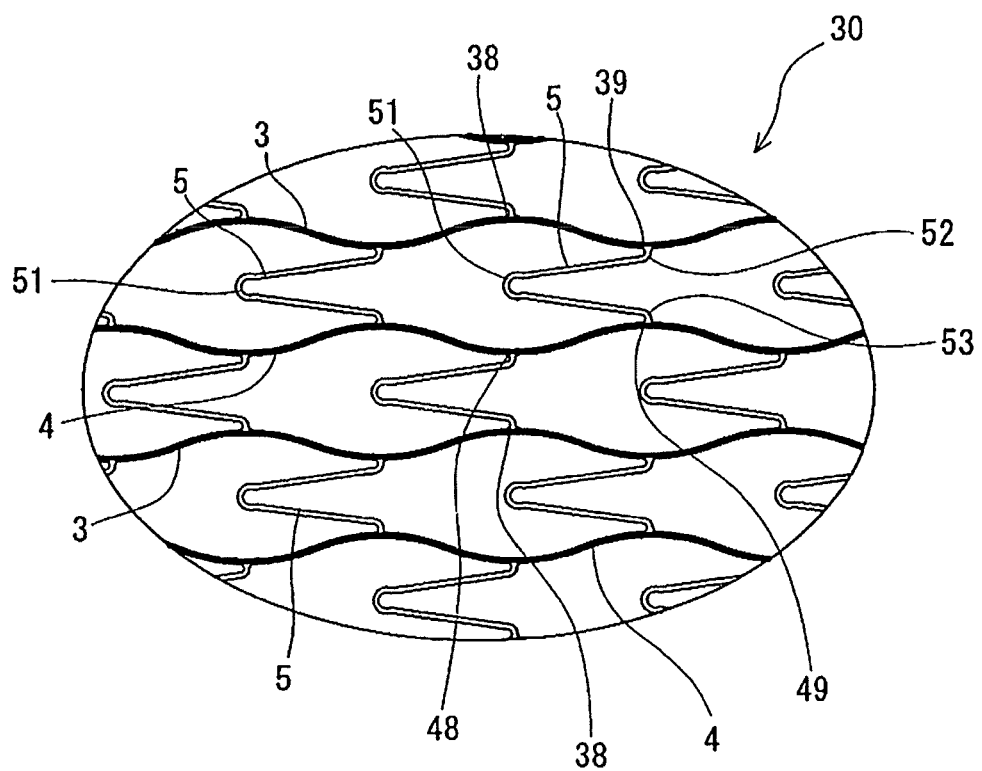
FIG. 8 is a partially enlarged view of a portion of the stent shown in FIG. 7.

FIGS. 7 and 8 illustrate a stent 30 according to yet another embodiment. The difference between the stent 30 of this embodiment and the above-described stent 1 involves the waveforms of the first wave-shaped struts 3 and the second wave-shaped struts 4. With the stent 30, the first wave-shaped strut 3 and the second wave-shaped strut 4 are each in a sinusoidal waveform. Other features of the stent according to this embodiment which are the same as in the above-described embodiments are identified by common reference numerals, and a detailed description of such features is not repeated.

In the stent 30 according to this embodiment, the first wave-shaped strut 3 and the second wave-shaped strut 4 possess substantially the same waveform. More particularly, the first wave-shaped struts 3 and the second wave-shaped struts 4 have substantially the same wavelength and substantially the same amplitude. The second wave-shaped struts 4 are axially shifted by about half a wavelength relative to the first wave-shaped struts 3.

Accordingly, as shown in FIG. 8, the circumferentially adjacent first wave-shaped struts 3 and second wave-shaped struts 4 are so arranged that an upper point 38 or lower point 39 of the first wave-shaped strut 3 and a lower point 48 or upper point 49 of the second wave-shaped strut 4 are substantially facing each other to form a closer section and a farther section. With stent of this embodiment, all of the respective wave-shaped struts 3 and 4 have the same length.

In the stent 30 according to this embodiment, both end portions 52, 53 of the connection strut 5 to be interconnected with the wave-shaped struts 3, 4 are in the form of an arcuate portion or small bent portion (part of a circle) curved in the outward direction of the connection strut 5. The connection strut 5 is interconnected, at this small bent portion, to the upper point 38 or lower point 39 and the lower point 48 or upper point 49 of the wave-shaped strut 3 and 4.

The stent 30 according to this embodiment also includes arcuate portions or small bent portions (part of a circle) 35a, 45a bent inwardly of the bent portion 9 on the proximal side by a predetermined distance relative to the bent portion 9 which is formed by combining the proximal portions of the first wave-shaped strut 3 and the second wave-shaped strut 4, thereby improving an expansion retention force of the bent portion 9 in the form of a relatively long free end.

Figure 9:
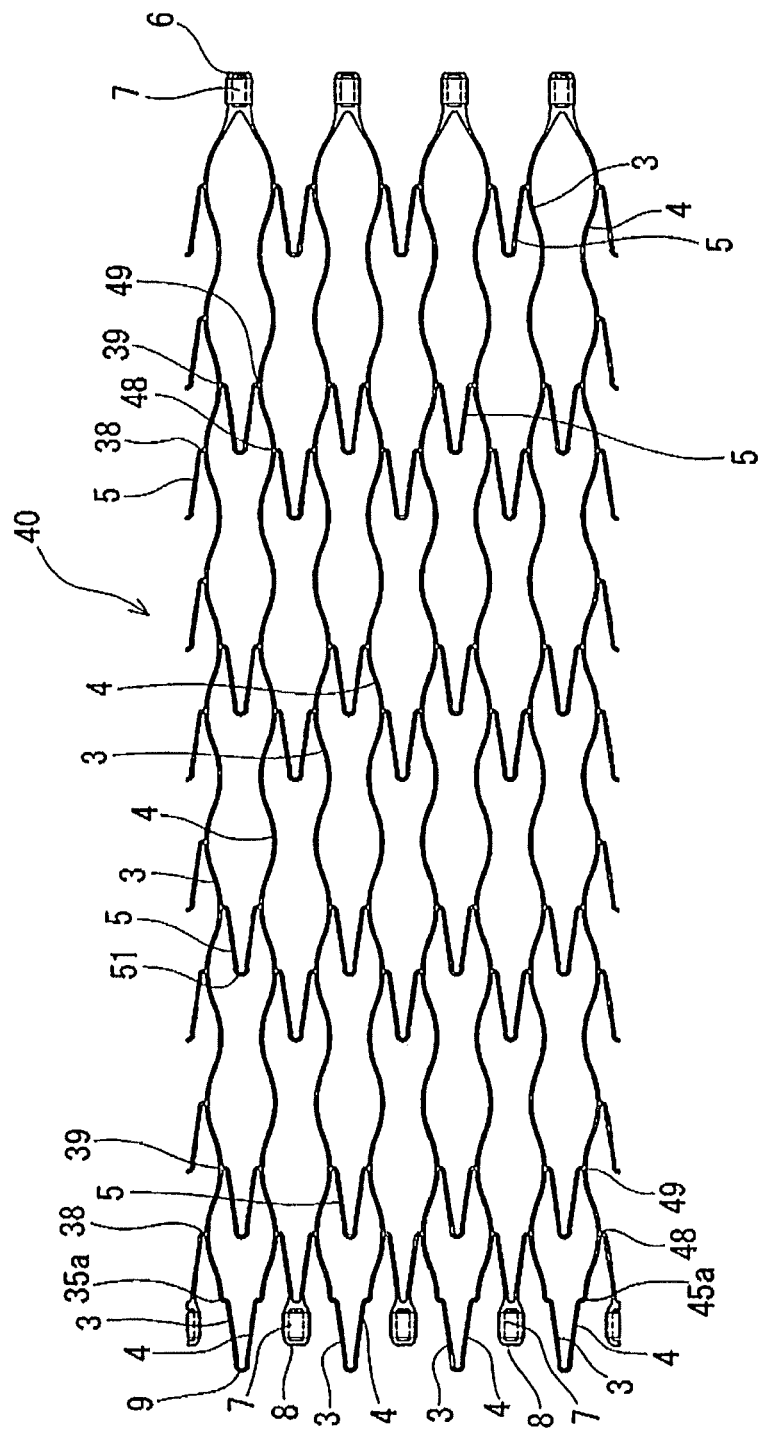
FIG. 9 is a development view of a stent for placement in living body according to a yet further embodiment disclosed here by way of example.

FIG. 9 illustrates a stent 40 for placement in living body according to a yet further embodiment. The difference between the stent 40 and the above-described stent 30 resides in the number of connection struts 5 provided between the first wave-shaped struts 3 and the second wave-shaped struts 4. With the above-stated strut 30, the connection strut 5 is provided at all the closer sections between the circumferentially adjacent first wave-shaped struts 3 and the second wave-shaped struts 4. In this stent 40, the connection strut 5 is provided at some of the closer sections between the circumferentially adjacent first wave-shaped struts 3 and the second wave-shaped struts 4. Specifically, the stent 40 has the connection strut 5 provided at alternate ones of the closer sections between the circumferentially adjacent first wave-shaped struts 3 and the second wave-shaped struts 4. The stent 40 is so arranged that the connection struts 5 are continuous along the circumferential direction, meaning they are circumferentially aligned with one another.

Figure 10:
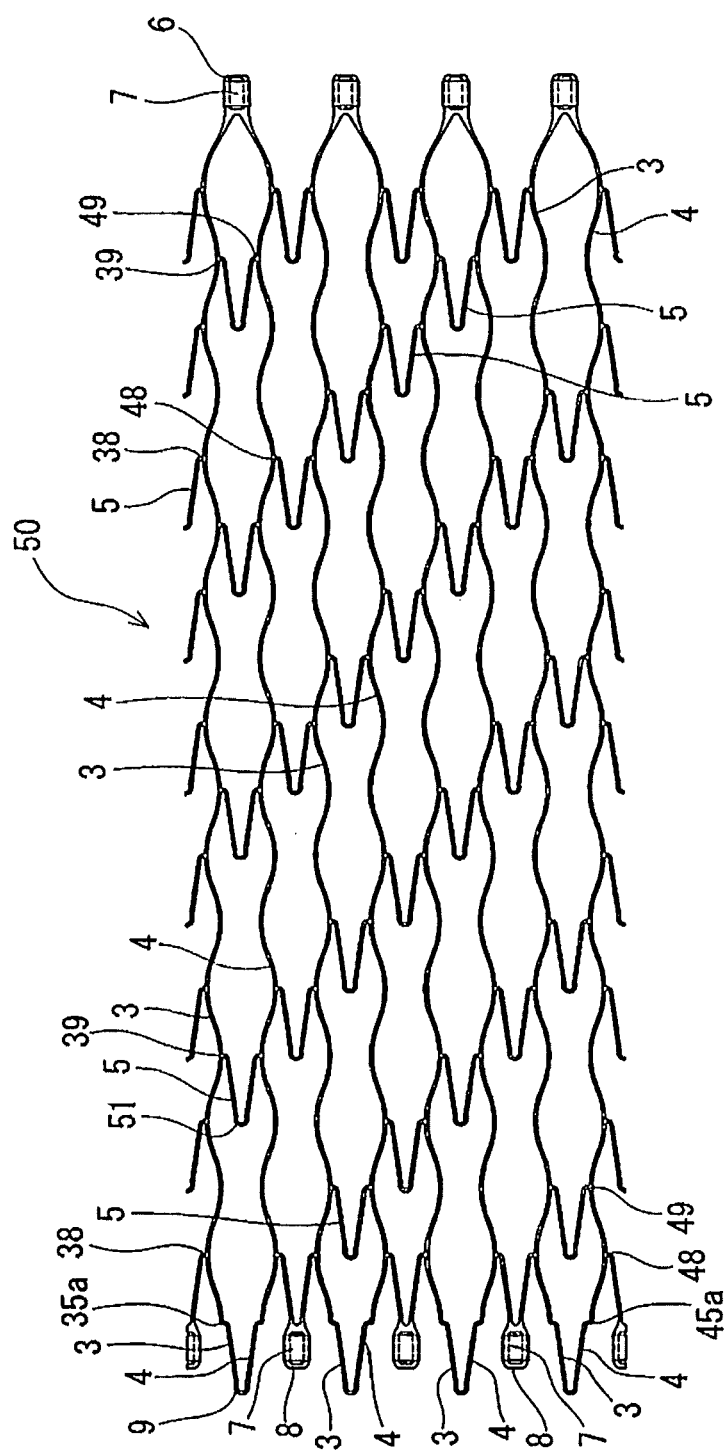
FIG. 10 is a development view of a stent for placement in living body according to still another embodiment disclosed here by way of example.

FIG. 10 shows a stent 50 according to still another embodiment. The stent 50 of this embodiment is the same as the above-stated stent 40 in that the connection strut 5 is provided at some, but not all, of the closer sections. In this stent 50, the connection struts 5 are located spirally along the circumferential direction. That is, the connection struts 5 between circumferentially adjacent wave-shaped struts 3, 4 are axially offset from one another.

In all the stents of the forgoing examples, the stent may contain physiologically active substances that are in a releasable condition (i.e., the substance can be released once the stent is indwelled in the body lumen of the living body). For causing a physiologically active substance to be releasable, there is mentioned, for example, a method wherein the stent surface is coated with a polymer (e.g. a biodegradable polymer) containing a physiologically active substance.

The biodegradable polymers are not critical provided that they are decomposed enzymatically or non-enzymatically in living bodies and the resulting decomposed matter does not exhibit toxicity. Usable examples include polylactic acid, polyglycolic acid, polylactic acid/polyglycolic acid copolymer, polycaprolactone, polylactic acid/polycaprolactone copolymer, polyorthoester, polyphosphazene, polyphosphoric ester, polyhydroxybutyric acid, polymalic acid, poly-α-amino acid, collagen, gelatin, laminin, heparan sulfate, fibronectin, vitronectin, chondroitin sulfate, hyaluronic acid, polypeptide, chitin, chitosan and the like.

As the physiologically active substance, there can be used, for example, substances promoting lysis or metabolism of thrombus or a thrombotic complex or substances inhibiting an increase of thrombus or a thrombotic complex, substances inhibiting intimal hypertrophy, anticancer drugs, immunosuppressors, antibiotic drugs, antirheumatic drugs, antithrombotic drugs, HMG-CoA reductase inhibitors, ACE inhibitors, calcium antagonist agents, antihyperlipidemic agents, anti-inflammatory agents, integrin inhibitors, antiallergic agents, antioxidants, GPIIbIIIa antagonists, retinoids, flavonoids and carotenoids, lipid improvers, DNA synthesis inhibitors, tyrosine kinase inhibitors, antiplatelet drugs, vascular smooth-muscle proliferation inhibitors, bioderived substances, interferon, epidermal cells prepared by biogenetics, and the like. The above substances may be used in admixture of two or more.

With regard to the substances promoting lysis or metabolism of thrombus or a thrombotic complex or substances inhibiting an increase of thrombus or a thrombotic complex, usable substances promoting lysis of thrombus or a thrombotic complex include, for example, streptokinase, a plasminogen activator, urokinase, staphylokinase, lumbrokinase, nattokinase, and analogues thereof. As the substance inhibiting the increase of thrombus or a thrombotic complex, there can be usable, for example, antiplatelet drugs or GP IIb/IIIa antagonists, typical of which are acetylsalicylic acid, ticlopidine, dipyridamole, cilostazol, beraprost Na, limaprost alfadex, ethyl icosapentate, sarpogrelate hydrochloride, Trapidil, Clopidogrel, prasugrel, and analogues thereof, and anticoagulants, typical of which are heparin and Warfarin potassium.

Preferred anticancer drugs include, for example, vincristine, vinblastine, vindesine, irinotecan, pirarubicin, paclitaxel, docetaxel, methotrexate and the like. Preferred immunosuppressors include, for example, sirolimus, tacrolimus, azathioprine, cyclosporine, cyclophosphamide, mycophenolate mofetil, gusperimus, mizoribine and the like. Preferred antibiotic drugs include, for example, mitomycin, adriamycin, doxorubicin, actinomycin, daunorubicin, idarubicin, pirarubicin, aclarubicin, epirubicin, peplomycin, zinostatin stimalamer and the like. Preferred antirheumatic drugs include, for example, methotrexate, sodium thiomalate, penicillamine, lobenzarit and the like. Preferred antithrombotic drugs include, for example, heparin, aspirin, antithrombin preparation, ticlopidine, hirudin and the like. Preferred HMG-CoA reductase inhibitors include, for example, cerivastatin, cerivastatin sodium, atorvastatin, nisvastatin, itavastatin, fluvastatin, fluvastatin sodium, simvastatin, lovastatin, pravastatin and the like. Preferred ACE inhibitors include, for example, quinapril, perindopril erbumine, trandolapril, cilazapril, temocapril, delapril, enalapril maleate, lisinopril, captopril and the like. Preferred calcium antagonist agents include, for example, nifedipine, nilvadipine, diltiazem, benidipine, nisoldipine and the like. Preferred antihyperlipidemic agents include, for example, probucol and the like. Preferred anti-allergic agents include, for example, tranilast and the like. Preferred retinoids include all-trans retinoic acid. Preferred flavonoids and carotenoids include catechins, particularly, epigallocatechin gallate, anthocyanin, proanthocyanidin, licopin, β-carotene and the like. Preferred tyrosine kinase inhibitors include, for example, genisteine, tyrphostin, erbstatin and the like. Preferred anti-inflammatory agents include, for example, salicylic acid, aspirin, acetoaminophen, phenacetin, indomethacin, diclofenac sodium, piroxicam, fenoprofen calcium, ibuprofen, chlorpheniramine maleate, diflunisal, dexamethasone, clobetasol propionate, diflorasone diacetate, difluprednate, betamethasone dipropionate, diflucortolone valerate, budesonide, fluocinonide, amcinonide, halcinonide, hydrocortisone butyrate dipropionate, mometasone furoate, betamethasone butyrate propionate, deprodone propionate, betamethasone valerate, beclomethasone propionate, fluocinolone acetonide, prednisolone valerate acetate, triamcinolone acetonide, flumethasome pivalate, clobetasone butyrate, hydrocortisone butyrate, prednisolone acetate, methylprednisolone acetate and the like. Preferred bio-derived substances include, for example, EGF (epidermal growth factor), VEGF (vascular endothelial growth factor), HGF (hepatocyte growth factor), PDGF (platelet derived growth factor), bFGF (basic fibroblast growth factor) and the like.

The stent disclosed here is preferably a so-called self-expandable stent possessing a substantially cylindrical form, is compressed in a direction of the central axis when inserted into a living body and is expanded outwardly when indwelled in the living body, thereby being restored to its original form before the compression. In case where such a self-expandable stent is provided, all the types of stents according to the above-described embodiments can be used.

The material forming the self-expandable stent is preferably a superelastic metal. For the superelastic metal, superelastic alloys are preferably used. The superelastic alloy used herein is generally called shape-memory alloy and means one that exhibits superelasticity at least at a living body temperature (about 37° C.). Especially, there are preferably used superelastic metals such as a Ti—Ni alloy having 49 to 53 atomic % of Ni, a Cu—Zn alloy having 38.5 to 41.5 wt % of Zn, a Cu—Zn—X alloy having 1 to 10 wt % of X (wherein X=Be, Si, Sn, Al or Ga), a Ni—Al alloy having 36 to 38 atomic % of Al and the like. More preferably, the above-indicated Ti—Ni alloy is used. Mechanical characteristics can be appropriately changed when using the Ti—Ni alloy, part of which is substituted with 0.01 to 10.0% of X (wherein X=Co, Fe, Mn, Cr, V, Al, Nb, W, B or the like) to provide a Ti—Ni—X alloy or using the Ti—Ni alloy, part of which is substituted with 0.01 to 30.0 atomic % of X (wherein X=Cu, Pb or Zr) to provide a Ti—Ni—X alloy, or when properly selecting a cold working rate and/or final thermal treatment conditions. In this regard, when using the above-indicated Ti—Ni—X alloy, its mechanical characteristics can be conveniently changed by properly selecting the cold working rate and/or final thermal treatment conditions. The buckling strength (yield stress under load) of a superelastic alloy used is preferably at 5 to 200 kg/mm2 (22° C.), more preferably at 8 to 150 kg/mm2, and the restoring stress (yield stress under load-removed conditions) is preferably at 3 to 180 kg/mm2 (22° C.), more preferably at 5 to 130 kg/mm2. The term "superelasticity" used herein means that even if deformations (bending, extending, compressing) are made to a region where an ordinary metal is plastically deformed at a use temperature, the original form before compression is substantially restored after release of deformations without need of heating.

In the stents according to all the embodiments described above, the diameter of the stent under non-expanded (or compressed) conditions is conveniently at 0.5 to 1.8 mm, preferably at 0.6 to 1.4 mm. The length of the stent under non-expanded (or non-compressed) conditions is conveniently at 5 to 200 mm, preferably at 8.0 to 100.0 mm. The diameter of the stent at the time of forming thereof (before compression) is conveniently at 1.5 to 6.0 mm, preferably at 2.0 to 5.0 mm. Moreover, the thickness of the stent is conveniently at 0.05 to 0.40 mm, preferably at 0.05 to 0.15 mm. The width of the wave-shaped struts is conveniently at 0.01 to 1.00 mm, preferably at 0.05 to 0.2 mm. The wave-shaped struts are preferably processed smoothly on the surface thereof, and smoothing with electrolytic polishing is more preferred. The radial strength of the stent is preferably at 0.1 to 30.0 N/cm, more preferably at 0.5 to 5.0 N/cm.

The stent described here may be a so-called balloon-expandable stent possessing a substantially cylindrical form, having a diameter sufficient to be inserted into a lumen in a living body and expandable radially outwardly when a force radially spreading from inside of the stent is applied to the stent. As such a balloon-expandable stent, the stents of the types described in all the embodiments above may be used.

The stent-forming materials for the balloon-expandable stent preferably have some degree of biocompatability. Possible stent-forming materials include, for example, stainless steels, tantalum or tantalum alloys, platinum or platinum alloys, gold or gold alloys, cobalt-based alloys such as cobalt chromium alloys. After fabrication of a stent configuration, noble metal plating (gold, platinum) may be carried out. Preferred stainless steels include SUS316L that is most resistant to corrosion.

The stent-forming material used for the balloon-expandable stent may be a biodegradable metal. As such a biodegradable metal, there may be used, for example, pure magnesium or magnesium alloys, calcium, zinc, lithium and the like. Preferably, pure magnesium or magnesium alloys are mentioned. Magnesium alloys are preferably those that are made of a principal component of magnesium and at least one element selected from biocompatible elements including Zr, Y, Ti, Ta, Nd, Nb, Zn, Ca Al, Li and Mn.

The magnesium alloys include, for example, ones that contain 50 to 98% of magnesium, 0 to 40% of lithium (Li), 0 to 5% of iron, and 0 to 5% of other metals or rare earth elements (cerium, lanthanum, neodymium, praseodymium and the like). Alternatively, there may be mentioned, for example, those containing 79 to 97% of magnesium, 2 to 5% of aluminum, 0 to 12% of lithium (Li), and 1 to 4% of rare earth elements (cerium, lanthanum, neodymium, praseodymium and the like). Still alternatively, there may be mentioned, for example, those containing 85 to 91% of magnesium, 2% of aluminum, 6 to 12% of lithium (Li) and 1% of rare earth elements (cerium, lanthanum, neodymium, praseodymium and the like). Yet alternatively, there may be mentioned, for example, those containing 86 to 97% of magnesium, 2 to 4% of aluminum, 0 to 8% of lithium (Li) and 1 to 2% of rare earth elements (cerium, lanthanum, neodymium, praseodymium and the like). Still yet alternatively, there may be mentioned, for example, those containing 8.5 to 9.5% of aluminum, 0.15 to 0.4% of manganese (Mn), 0.45 to 0.90% of zinc and the balance being magnesium. Alternatively, there may be mentioned, for example, those containing 4.5 to 5.3 of aluminum, 0.28 to 0.5% of manganese (Mn) and the balance being magnesium. Still alternatively, there may be mentioned, for example, those containing 55 to 65% of magnesium, 30 to 40% of lithium (Li), and 0 to 5% of other metals and/or rare earth elements (cerium, lanthanum, neodymium, praseodymium and the like).

The stent is preferably chamfered. The stent can be chamfered by chemically, electrolytically or mechanical polishing after formation of the stent in a final shape.

Further, it is preferred to anneal a stent after forming into a final shape. The annealing leads to improved flexibility and plasticity of the stent on its entirety, thereby helping to ensure good indwelling properties in a bended blood vessel. When compared with the case where no annealing is carried out, the annealed stent can reduce a force of restoration to an original shape after expansion of the stent and a linearly restoring force developed at the time when the stent is expanded at a bended blood vessel portion, and can also reduce physical stimulation imparted to inner walls of bended blood vessel and a factor of restenosis. Preferably, the annealing is carried out in such a way that in order not to cause an oxide film to be formed on the stent surface, the stent is heated in an atmosphere of an inert gas (e.g. a mixed gas of nitrogen and hydrogen) to 900 to 1200° C. and quenching.

Further, the stents according to all the foregoing embodiments may be processed to provide micro grooves or micro holes so as to facilitate the stability of plaque or may be attached with proteins, drugs or genes.

Next, a stent delivery system (i.e. living organ dilator) used to deliver the stents described above will be described with reference to FIGS. 11 and 12. A stent delivery system 200 according to this example includes a sheath 202, a stent 201 accommodated in a distal end portion of the sheath 202, and an inner tube 204 that is slidably inserted into the sheath 202 so as to release the stent 201 from the distal end of the sheath 202.

The stent 201 used in the stent delivery system 200 can be a self-expandable stent such as set out above, which is formed in a cylindrical form and can be compressed in a direction of a central axis when inserted into a living body and expanded outwardly when indwelled in the living body thereby restoring the original form before the compression. As the form of stent, it is preferred to use one having such a form of the foregoing stent 1. This stent 1 is accommodated in the sheath in such a state that the bulge portion 8 is disposed at a distal end side and the connection portion 6 is disposed at a proximal portion.

Figure 11:
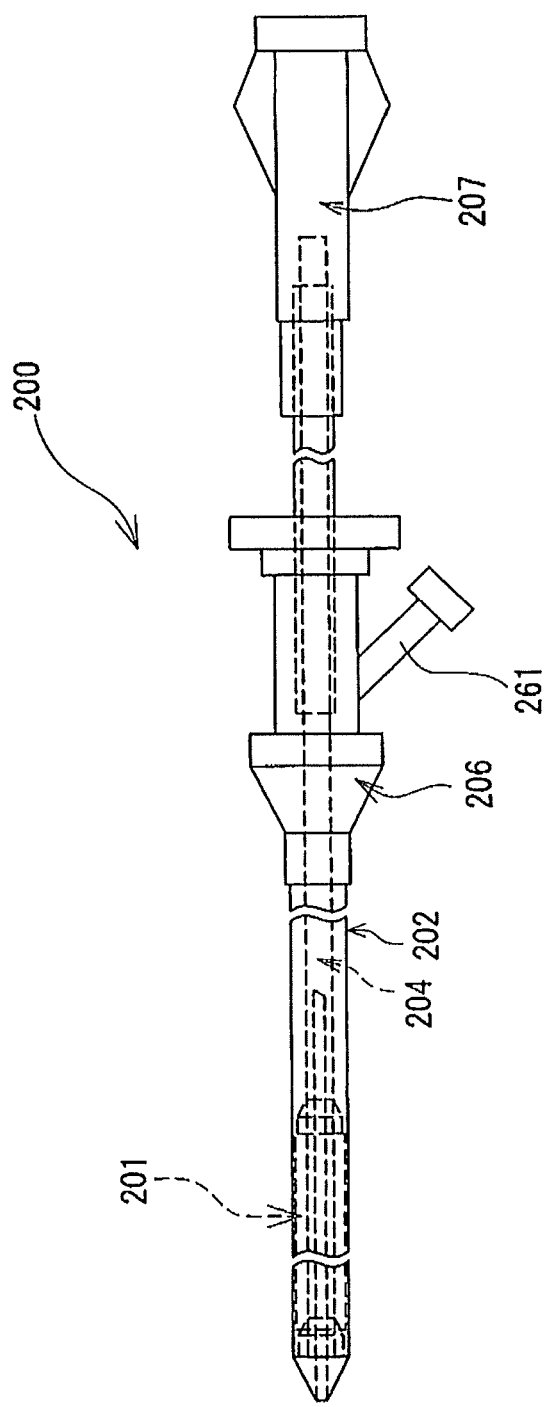
FIG. 11 is a front view, partially omitted, of a stent delivery system according to one embodiment disclosed by way of example.
Figure 12:
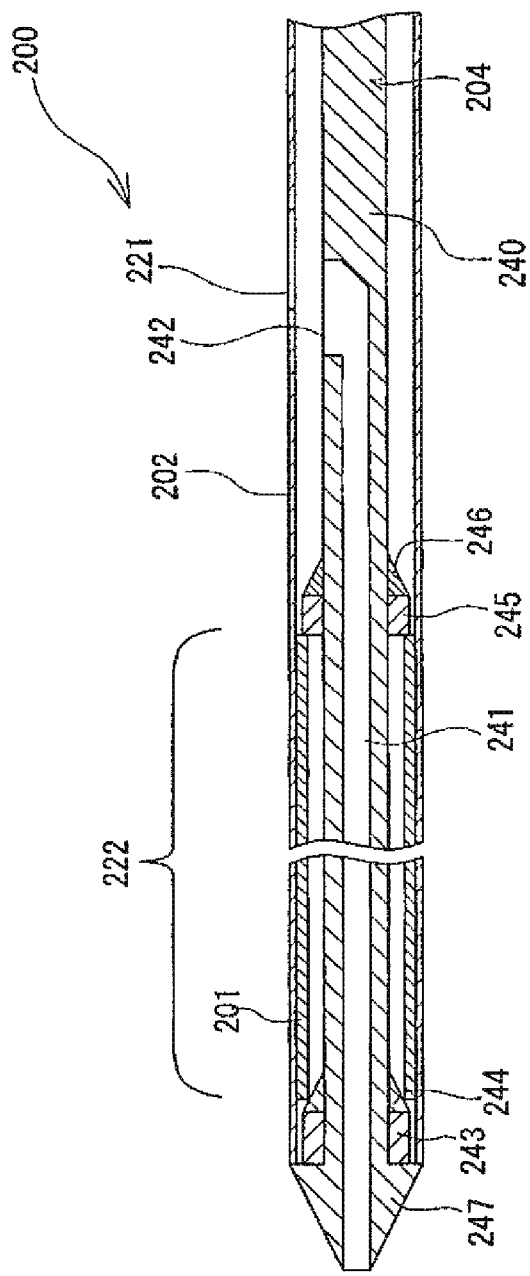
FIG. 12 is an enlarged, longitudinal cross-sectional view of a distal portion of the stent delivery system shown in FIG. 11.

The stent delivery system 200 according to the example is provided with the sheath 202, the self-expandable stent 201 and the inner tube 204 as shown in FIG. 11. As shown in FIGS. 11 and 12, the sheath 202 is a tubular body, and is opened at both the distal and proximal ends of the sheath 202. The distal end opening functions as a release port of the stent 201 when the stent 201 is indwelled at a stenosed portion in a living body lumen. When released from the distal end opening, the stent 201 is expanded by removal of the stress load exerted thereon and is restored to its form before compression. The distal portion of the sheath 202 corresponds to a stent accommodation portion 222 wherein the stent 201 is accommodated. The sheath 202 is provided with a side hole 221 at the proximal side of the accommodation portion 222. The side hole 221 allows a guide wire to be led outside.

When the sheath 202 is moved toward the distal end side relative to the stent 201, the stent 201 is compressed in a direction of its central axis and can be accommodated in the distal portion of the sheath 202.

The outer diameter of the sheath 202 is preferably 0.5 to 4.0 mm, more preferably 0.8 to 3.0 mm. The inner diameter of the sheath is preferably 0.5 to 2.5 mm and the length of the sheath 202 is preferably 300 to 2500 mm, more preferably 300 to 2000 mm.

A sheath hub 206 is fixed at the proximal end portion of the sheath 202 as shown in FIG. 11. The sheath hub 206 includes a sheath hub body and a valve that is accommodated in the sheath hub body so as to hold the inner tube 204 in slidable and a fluid-tight condition. The sheath hub 206 is also provided with a side port 261 obliquely branched from the vicinity of the center of the sheath hub body. The sheath hub 206 is preferably provided with an inner tube lock mechanism restricting the movement of the inner tube 204.

As shown in FIGS. 11 and 12, the inner tube 204 includes a shaft-shaped inner tube body 240, a distal end portion 247 provided at a distal end of the inner tube body 240 and projecting beyond the distal end of the sheath 202, and an inner tube hub 207 fixed at the proximal end portion of the inner tube body 240.

It is preferred that the distal end portion 247 projects beyond the distal end of the sheath 202 and is so formed as to be radially, gradually reduced in outer diameter and tapered toward the distal end as shown in FIG. 12. Such formation allows relatively easy insertion into a stenosed portion. Preferably, the inner tube 204 is provided with a stopper at the distal side of the stent 201 which inhibits the movement of the sheath 202 toward the distal end. The proximal end of the distal end portion 247 of the inner tube 204 enables contact with the distal end of the sheath 202 and functions as such a stopper.

As shown in FIG. 12, the inner tube 204 is provided with two projections 243, 245 so as to hold the self-expandable stent 201 therewith. The projections 243 and 245 are preferably ring-shaped (annular) projections. The stent hold projection 243 is provided at the proximal side of the distal end portion 247 of the inner tube 204. The stent release projection 245 is proximal of the stent hold projection 243 and is spaced apart by a predetermined distance from the stent hold projection 243. The stent 201 is placed between these two projections 243, 245. The outer diameter of these projections 243, 245 are set at a size sufficient to allow contact with the stent 201 in a compressed condition described hereinafter. Accordingly, the stent 201 is restricted with respect to its movement toward the distal direction by the projection 243 and also with respect to the movement toward the proximal direction by the projection 245. Moreover, when the sheath 202 is moved toward the proximal direction, the stent 201 stays at its position by virtue of the projection 245 and is exposed from the sheath 202 and released. As shown in FIG. 12, the proximal end of the stent release projection 245 preferably has a tapered portion 246 that is gradually reduced in outer diameter toward the proximal end. Likewise, it is preferred that the proximal end side of the stent hold projection 243 has a tapered portion 244 that is gradually reduced in outer diameter toward the proximal end portion as shown in FIG. 12. The inner tube 204 can thus project beyond the distal end of the sheath 202 to release the stent 201 from the sheath, after which when the inner tube 204 is again accommodated in the sheath 202, the projection is prevented from being caught by the distal end of the sheath. The projections 243, 245 may be formed of a separate member made of a radiopaque material. This permits the position of the stent to be accurately observed under radioscopy, thus making the procedure easier.

As shown in FIG. 12, the inner tube 204 is provided with a lumen 241 extending from the distal end toward the proximal direction, at least proximally beyond the stent accommodation portion 222 of the sheath 202, and an inner tube side hole 242 communicating with the lumen 241 at the proximal side of the stent accommodation portion. With the stent delivery system 200 according to this example, the lumen 241 terminates at a formation portion of the side hole 242. The lumen 241 allows one end of a guide wire to be inserted from the distal end of the stent delivery system 200 and partially inserted through the inner tube, followed by leading out from the side face of the inner tube to the outside. The inner tube side hole 242 is located slightly to the distal side of the sheath side hole 221. The center of the inner tube side hole 242 is preferably located 0.5 to 10 mm on the distal side of the center of the sheath side hole 221.

The lumen 241 in the stent delivery system is not limited to the above-described construction. The lumen 241 may extend to the proximal end of the inner tube. In this case, the side hole 221 of the sheath is unnecessary.

The inner tube 204 passes through the sheath 202 and projects beyond the proximal end opening of the sheath 202. The inner tube hub 207 is fixedly secured, as shown in FIG. 11, at the proximal end portion of the inner tube 204.

Figure 13:
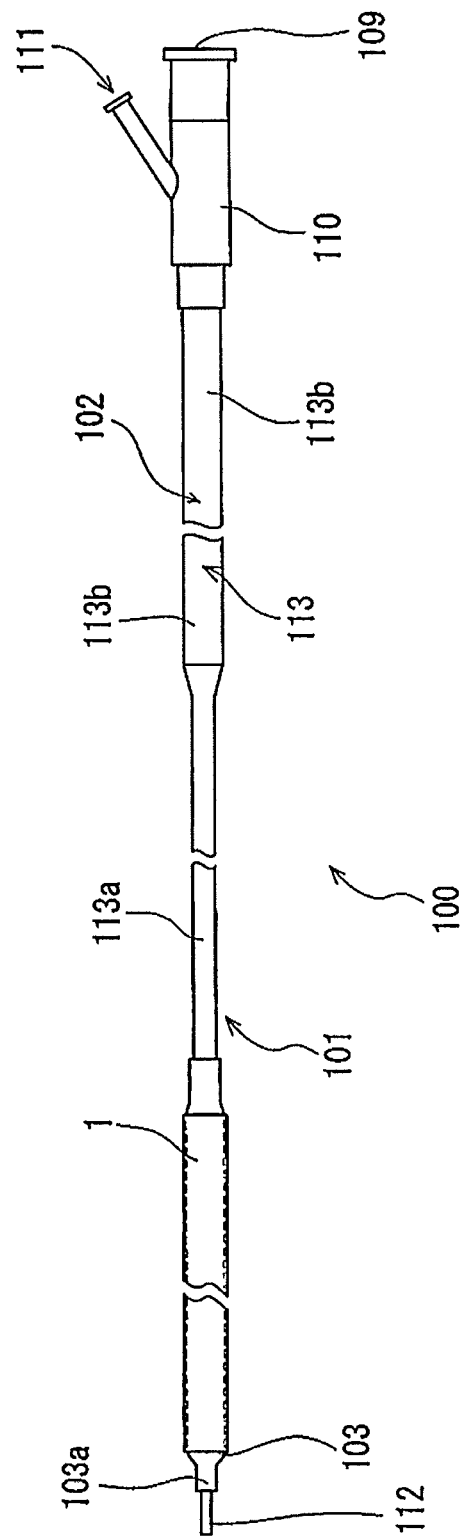
FIG. 13 is a front view of a stent delivery system according to another embodiment disclosed by way of example.
Figure 14:
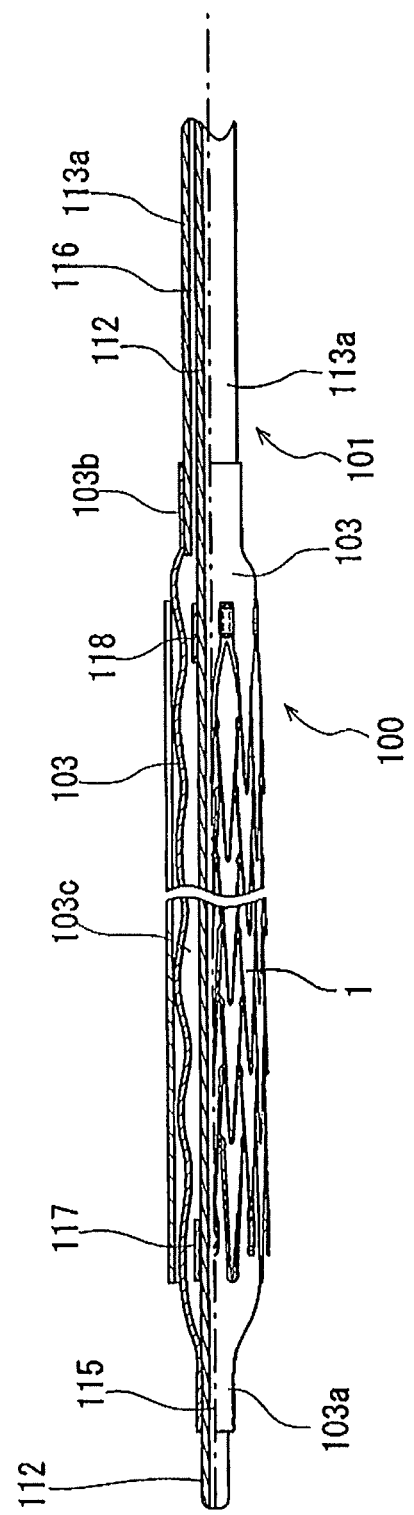
FIG. 14 is an enlarged, longitudinal cross-sectional view of a distal portion of the stent delivery system shown in FIG. 13.
Figure 15:
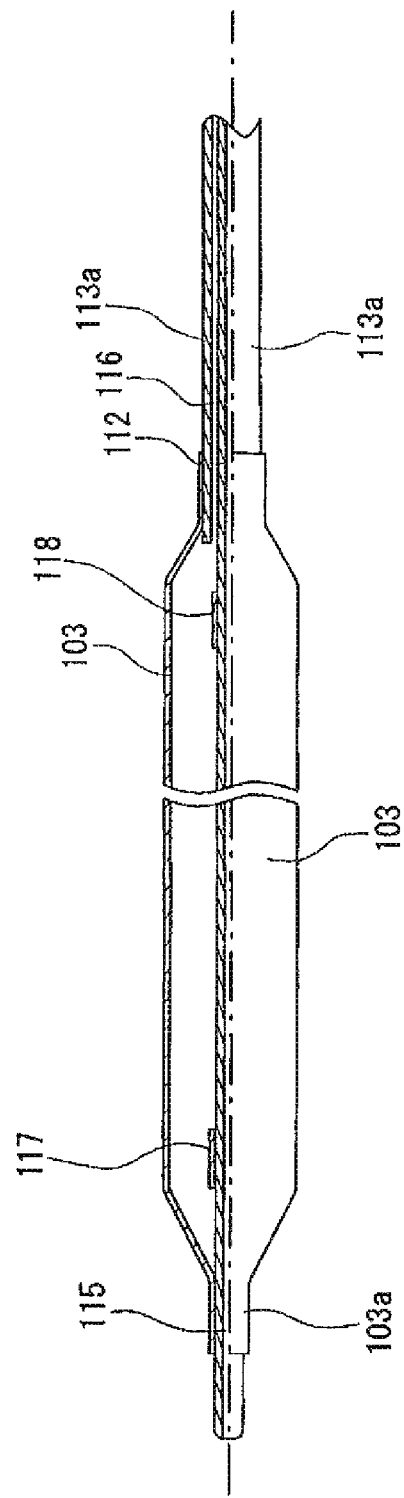
FIG. 15 is an illustrative view illustrating operations of the stent deliver system according to another embodiment disclosed here.

FIGS. 13-15 illustrate another type of stent delivery system 100. This stent delivery system 100 includes a tubular shaft body 102, a foldable and dilatable balloon 103 at the distal portion of the shaft body 102, and a stent 1 disposed to enclose or surround the balloon 103 in a folded state and expand when the balloon 103 is dilated.

The stent 1 used in the stent delivery system 100 may be any of the above-described stents 1.

The stent delivery system 100 according to this example is made up of the above-stated stent 1 and a tubular stent delivery system body 101 on which the stent 1 is mounted.

The stent delivery system body 101 includes the tubular shaft body 102 and the foldable and dilatable balloon 103 provided at the distal portion of the shaft body, and the stent 1 is mounted so as to enclose the folded balloon 103 and is expanded through dilation of the balloon 103.

As the stent 1, there may be used any of the stents of all the foregoing embodiments. The stent used here is a so-called balloon-expandable stent wherein it has a diameter sufficient to be inserted into a lumen in a living body and is expandable when a force radially spreading from inside of the stent is exerted on the stent.

With the stent delivery system 100 according to this example, the shaft body 102 is provided, as shown in FIGS. 13 and 14, with a guide wire lumen 115, which is open at one end at the distal end of the shaft body 102 and is also open at the other end at the proximal end portion of the shaft body 102.

This stent delivery system body 101 is provided with the shaft body 102 and the stent expanding balloon 103 attached at the distal end portion of the shaft body 102, and the stent 1 is mounted on the balloon 103. The shaft body 102 includes an inner tube 112, an outer tube 113 and a branched hub 110.

The inner tube 112 is a tubular body having the guide wire lumen 115 for inserting the guide wire through inside the tubular body as shown in FIGS. 13 and 14. The inner tube 112 is one, which preferably has, for example, a length of 100 to 2500 mm, more preferably 250 to 2000 mm, an outer diameter of 0.1 to 1.0 mm, more preferably 0.3 to 0.7 mm, and a thickness of 10 to 250 µm, more preferably 20 to 100 µm. The inner tube 112 is inserted into the outer tube 113 and the distal end of the inner tube 112 projects distally beyond the distal end of the outer tube 113. A balloon dilating lumen 116 is formed of the outer surface of the inner tube 112 and the inner surface of the outer tube 113 and has an adequate capacity for expanding the balloon. The outer tube 113 is a tubular body, which has the inner tube 112 inserted therein, with its distal end located at a slightly proximally of the distal end of the inner tube 112.

The outer tube 113 preferably has, for example, a length of 100 to 2500 mm, more preferably 250 to 2000 mm, an outer diameter of 0.5 to 1.5 mm, more preferably 0.7 to 1.1 mm, and a thickness of 25 to 200 µm, more preferably 50 to 100 µm.

With the stent delivery system 100 according to this example, the outer tube 113 includes a distal side outer tube 113a and a body side outer tube 113b, which are joined together. The distal side outer tube 113a is reduced in outer diameter in the form of a taper at a distal side portion relative to the joint with the body side outer tube 113b, so that the portion at the distal side extending from this tapered portion is smaller in outer diameter.

The outer diameter of the small diameter portion of the distal side outer tube 113a is 0.50 to 1.5 mm, preferably 0.60 to 1.1 mm. The outer diameters of the proximal end portion of the distal end side outer tube 113a and the body side outer tube 113b are, respectively, 0.75 to 1.5 mm, preferably 0.9 to 1.1 mm.

The balloon 103 has a distal end joint 103a and a proximal end joint 103b, and the distal end joint 103a is attached to the distal end of the inner tube 112 at a position slightly proximal of distal-most end of the inner tube 112. The proximal side joint 103b is attached to the distal end of the outer tube 113. The balloon 103 communicates with the balloon expanding dilating 116 in the vicinity of the proximal end of the balloon.

The materials for forming the inner tube 112 and outer tube 113 preferably have some degree of flexibility and include, for example, thermoplastic resins such as polyolefins (e.g. polyethylene, polypropylene, ethylene-propylene copolymer, ethylene-vinyl acetate copolymer and the like), polyvinyl chloride, polyamide elastomers, polyurethane and the like, silicone rubbers, latex rubbers and the like. Preferably, thermoplastic resins are used, of which polyolefins are more preferred.

The balloon 103 is foldable as shown in FIG. 14 and can be folded about the circumference of the inner tube 112 in a non-dilated state. As shown in FIG. 14, the balloon 103 has a dilatable portion in the form of a tubular portion having substantially the same diameter throughout (preferably, a cylindrical portion) so as to cause a mounted stent 1 to be outwardly expanded. The substantially cylindrical portion may not be a complete cylinder, but may be in a polygonal form. As stated above, the balloon 103 is attached in a liquid-tight manner to the inner tube 112 at the distal side joint 103a and is also attached in a liquid-tight manner to the distal end of the outer tube 113 at the proximal side joint 103b by an adhesive or by thermal melting. This balloon 103 is formed as tapered between the dilatable portion and the joints.

The balloon 103 is formed with a dilation space 103c between the inner surface of the balloon 103 and the outer surface of the inner tube 112. This dilation space 103c communicates with the dilation lumen 116 along the entire circumference at the proximal end portion. In this way, since the proximal end of the balloon 103 communicates with the dilation lumen having a relatively large capacity, injection of a dilation fluid from the dilation lumen 116 into the balloon can be reliably made.

The materials for forming the balloon 103 are preferably those having some extent of flexibility and include, for example, thermoplastic resins such as polyolefins (e.g. polyethylene, polypropylene, ethylene-propylene copolymer, ethylene-vinyl acetate copolymer, crosslinking ethylene vinyl acetate copolymer and the like), polyvinyl chloride, polyamide elastomers, polyurethanes, polyesters (e.g. polyethylene terephthalate), polyarylene sulfides (e.g. polyphenylene sulfide) and the like, silicone rubbers, latex rubbers and the like. Especially, stretchable materials are preferred, and the balloon 103 is preferably made of biaxially stretched one having high strength and dilation force.

The sizes of the balloon 103 are such that an outer diameter of a dilated cylindrical portion (a dilatable portion) is 2 to 4 mm, preferably 2.5 to 3.5 mm, and the length of the cylindrical portion is slightly larger than with the stent used and is conveniently 5 to 200 mm, preferably 8.0 to 100.0 mm. The outer diameter of the distal end side joint 103a is 0.9 to 1.5 mm, preferably 1 to 1.3 mm, and the length is 1 to 5 mm, preferably 1 to 3 mm. The outer diameter of the proximal end side joint 103b is 1 to 1.6 mm, preferably 1.1 to 1.5 mm, and the length is 1 to 5 mm, preferably 2 to 4 mm.

The stent delivery system 100 is, as shown in FIGS. 14 and 15, provided with two radiopaque members 117 and 118 fixed to the outer surface of the shaft body at positions corresponding to the opposite ends of the dilated cylindrical portion (dilatable portion). It will be noted that two radiopaque members may be provided as fixed to the outer surface of the shaft body 102 (i.e. the inner tube 112 in this example) at positions corresponding to the opposite ends of a predetermined length of a central portion of the stent 1. Moreover, a single radiopaque member, which is fixed to the outer surface of the shaft body at a position corresponding to the central portion of the stent, may also be provided.

Preferably, the radiopaque members 117 and 118 are in the form of a ring having a predetermined length or are made of a spirally wound wire. The formation materials preferably include gold, platinum, tungsten or alloys thereof, silver-palladium alloys and the like.

The stent 1 is mounted so as to enclose the balloon 103. The stent is made by processing a metal pipe whose inner diameter is larger than an outer diameter of a folded balloon and is smaller in diameter than in the case where the stent is expanded. The balloon is inserted into the stent made above, in which a uniform force is inwardly exerted on the outer surface of the stent to reduce the diameter thereof thereby providing a stent in the form of a product. That is, the stent 1 is completed by being mounted on the balloon under compression.

A linear rigidity-imparting body may be inserted between the inner tube 112 and the outer tube 113 (into the balloon dilating lumen 116). The rigidity-imparting body inhibits or prevents the body 102 of the stent delivery system 100 from being excessively bent at a bended portion and permits the distal portion of the stent delivery system 100 to be readily pushed in without much lowering of the flexibility of the stent delivery system 100. The distal end portion of the rigidity-imparting body is preferably smaller in outer diameter than other portions using a method such as of polishing. The smaller diameter distal end of the rigidity-imparting body preferably extends to the vicinity of the distal end portion of the outer tube 113. The rigidity-imparting body is preferably made of a metal wire, including an elastic metal wire, such as a stainless steel wire or the like, or a superelastic metal wire with its diameter being 0.05 to 1.50 mm, preferably 0.10 to 1.00 mm. More preferably, there are mentioned high-tensile stainless steel wires for spring and superelastic alloy wires.

With the stent delivery system 100 according to this example, a branch hub 110 is fixed to the proximal end as shown in FIG. 13. The branch hub 110 has a guide wire introduction port 109, which communicates with a guide wire lumen 115 to form a guide wire port. The branch hub 110 is formed of an inner tube hub fixed to the inner tube 112 and an outer hub which communicates with a balloon dilation lumen 116, which has an injection port 111 and which is fixed to the outer tube 113. The outer tube hub and the inner tube hub are fixedly secured together. The material forming the branch hub 110 preferably include thermoplastic resins such as polycarbonate, polyamide, polysulfone, polyarylate, methacrylate-butylene-styrene copolymer and the like.

The structure of the stent delivery system is not limited to those set forth above, but may be one that has a guide wire insertion port communicating with the guide wire lumen at an intermediate portion of the stent delivery system.

The detailed description above describes features and aspects of embodiments of a stent described as examples of the invention disclosed here. The invention is not limited, however, to the precise embodiments and variations described. Changes, modifications and equivalents can be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent for placement in a living body, the stent comprising:
   a plurality of axially extending wave-shaped struts which are circumferentially arranged in a substantially cylindrical form, each of the plurality of wave-shaped struts extending in an axial direction from one axial end of the stent to an opposite axial end of the stent;
   each of the axially extending wave-shaped struts possessing a plurality of alternating and axially spaced apart points, the points including upper points which are mountains of the wave-shaped strut, the points also including lower points which are valleys of the wave-shaped strut;
   the points on each of the axially extending wave-shaped struts being circumferentially aligned with points on others of the axially extending wave-shaped struts;
   at least some of the circumferentially aligned points in each pair of circumferentially adjacent wave-shaped struts being located in closer sections of the stent, and at least some of the circumferentially aligned points in each pair of the circumferentially adjacent wave-shaped struts being located in farther sections of the stent;
   the points of the circumferentially adjacent wave-shaped struts located in the closer sections being positioned closer together than the points of the circumferentially adjacent wave-shaped struts located in the farther sections;
   a plurality of connection struts interconnecting the axially extending wave-shaped struts which are circumferentially adjacent so that every pair of axially extending wave-shaped struts which are circumferentially adjacent one another are interconnected by at least one of the connection struts, the connection struts each having a center;
   each connection strut interconnecting the axially extending wave-shaped struts at the closer section;
   each connection strut including two linear segments and a bent center portion positioned between the two linear segments, the bent center portion of each connection strut extending in an axial direction of the stent;
   the closer sections comprising first closer sections and second closer sections;

the connection struts comprising first connection struts and second connection struts;

the plurality of wave-shaped struts including a plurality of first wave-shaped struts and a plurality of second wave-shaped struts, each of the second wave-shaped struts being positioned circumferentially between two of the first wave-shaped struts;

the plurality of first wave-shaped struts each including a plurality of the upper points and a plurality of the lower points, the plurality of second wave-shaped struts each including a plurality of the upper points and a plurality of the lower points;

the upper points of each first wave-shaped strut and the lower points of a first respective circumferentially adjacent one of the second wave-shaped struts being substantially in face-to-face relation with each other and forming the first closer sections;

the lower points of each first wave-shaped strut and the upper points of a second respective circumferentially adjacent one of the second wave-shaped struts being substantially in face-to-face relation with each other and forming the second closer sections;

the first connection struts interconnecting all of the upper points of the first wave-shaped struts and all of the lower points of the second wave-shaped struts which form the first closer sections; and the second connection struts interconnecting all of the lower points of the first wave-shaped struts and all of the upper points of the second wave-shaped struts which form the second closer sections.

2. The stent for placement in a living body as defined in claim 1, the first wave-shaped struts circumferentially alternating with the second wave-shaped struts so that one of the second wave-shaped struts is located between each pair of circumferentially closest first wave-shaped struts, and so that one of the first wave-shaped struts is located between each pair of circumferentially closest second wave-shaped struts, each of the first wave-shaped struts and the second wave-shaped struts have substantially the same wavelength and substantially the same amplitude, and the second wave-shaped struts are shifted in an axial direction of the stent so that the upper points on the first wave-shaped struts are not circumferentially aligned with the upper points on the second wave-shaped struts.

3. A stent for placement in a living body, the stent comprising:

a plurality of axially extending wave-shaped struts each extending in an axial direction from one end of the stent to an other end of the stent and arranged in a circumferential direction, and a plurality of connection struts interconnecting circumferentially adjacent wave-shaped struts so that every pair of axially extending wave-shaped struts which are circumferentially adjacent one another are interconnected by at least one of the connection struts, wherein the circumferentially adjacent wave-shaped struts include a plurality of closer sections at which circumferentially aligned portions of the circumferentially adjacent wave-shaped struts are located relatively closer together, and wherein the circumferentially adjacent wave-shaped struts include a plurality of farther sections at which circumferentially aligned portions of the circumferentially adjacent wave-shaped struts are located relatively farther apart, the connection struts interconnecting the adjacent wave-shaped struts at the closer sections, and each connection strut including two linear segments and a bent center portion positioned between the two linear segments, the bent center portion extending in an axial direction of the stent;

the closer sections comprising first closer sections and second closer sections;

the connection struts comprising first connection struts and second connection struts;

the plurality of wave-shaped struts including a plurality of first wave-shaped struts and a plurality of second wave-shaped struts, each of the second wave-shaped struts being positioned circumferentially between two of the first wave-shaped struts;

the plurality of first wave-shaped struts each including a plurality of upper points and a plurality of lower points, the plurality of second wave-shaped struts each including a plurality of upper points and a plurality of lower points;

the upper points of each first wave-shaped struts and the lower points of a first respective circumferentially adjacent one of the second wave-shaped struts being substantially in face-to-face relation with each other and forming the first closer sections;

the lower points of each first wave-shaped strut and the upper points of a second respective circumferentially adjacent one of the second wave-shaped struts being substantially in face-to-face relation with each other and forming the second closer sections;

the first connection struts interconnecting all of the upper points of the first wave-shaped struts and all of the lower points of the second wave-shaped struts which form the first closer sections; and the second connection struts interconnecting all of the lower points of the first wave-shaped struts and all of the upper points of the second wave-shaped struts which form the second closer sections.

4. The stent for placement in a living body as defined in claim 3, wherein the bent center portion of the connection strut is a free end of the connection strut which extends toward a distal end of the stent.

5. The stent for placement in a living body as defined in claim 3, the farther sections comprising first farther sections and second farther sections;

the lower points of the each first wave-shaped struts and the upper points of the first respective circumferentially adjacent one of the second wave-shaped struts being substantially in face-to-face relation with each other and forming the first farther sections;

the upper points of the each first wave-shaped struts and the lower points of the second respective circumferentially adjacent one of the second wave-shaped struts being substantially in face-to-face relation with each other and forming the second farther sections; and the bent center portion of each connection strut being located in a vicinity of a respective farther section.

6. The stent for placement in a living body as defined in claim 3, wherein substantially all of the closer sections of the circumferentially adjacent first and second wave-shaped struts are interconnected with the connection struts.

7. The stent for placement in a living body as defined in claim 3, wherein the first wave-shaped struts, respectively, have substantially the same waveform except for both side portions of the first wave-shaped struts.

8. The stent for placement in a living body as defined in claim 3, wherein the second wave-shaped struts, respectively, have substantially the same waveform except for both end portions of the second wave-shaped struts.

9. The stent for placement in a living body as defined in claim 3, wherein the first wave-shaped struts possess substantially the same wavelength and substantially the same amplitude as the second wave-shaped struts, and each of the second wave-shaped struts is shifted relative to the first wave-shaped struts by about half a wavelength in the axial direction of the stent.

10. The stent for placement in a living body as defined in claim 3, wherein the first wave-shaped struts and the second wave-shaped struts extend substantially parallel to a central axis of the stent.

11. The stent for placement in a living body as defined in claim 3, wherein a plurality of the connection struts are provided between each pair of circumferentially adjacent wave-shaped struts and are arranged linearly along the axial direction of the stent.

12. The stent for placement in a living body as defined in claim 3, wherein a plurality of the connection struts extend along a circumferential direction of the stent.

13. The stent for placement in a living body as defined in claim 3, wherein the stent includes arcuate portions in a vicinity of a connection portion at which the wave-shaped struts are interconnected with the connection struts.

14. The stent for placement in a living body as defined in claim 3, wherein a surface of the stent is configured to promote endothelialization.

15. The stent for placement in a living body as defined in claim 3, wherein the stent possesses a substantially cylindrical form, and is configured to be compressed in a direction of a central axis of the stent when inserted into a living body and expanded outwardly when indwelled in the living body to restore its form before compression.

16. A stent delivery system comprising a sheath, the stent recited in claim 15 accommodated in a distal end portion of the sheath, and an inner tube slidably inserted into the sheath and configured to release the stent from a distal end of the sheath by movement toward a proximal end of the sheath.

17. The stent delivery system as defined in claim 16, wherein the stent is compressed in a direction of the central axis of the stent when the sheath is moved in a distal direction relative to the stent and is configured to be accommodated in the distal end portion of the sheath.

18. The stent for placement in a living body as defined in claim 3, wherein the stent possesses a substantially tubular form, has an outer diameter permitting insertion of the stent into a lumen in living body, and is configured to expand when a radially outwardly directed spreading force is exerted on the stent from inside of the stent.

19. A stent delivery system comprising a tubular shaft body, a foldable and dilatable balloon provided at a distal portion of the shaft body, and the stent recited in claim 18, the stent surrounding the balloon while in a folded state and radially outwardly expandable by dilation of the balloon.

* * * * *